(12) United States Patent
Hoff et al.

(10) Patent No.: US 7,833,771 B2
(45) Date of Patent: Nov. 16, 2010

(54) POLYPEPTIDES HAVING ALPHA-AMYLASE ACTIVITY AND POLYNUCLEOTIDES ENCODING SAME

(75) Inventors: Tine Hoff, Holte (DK); Carsten Andersen, Vaerlose (DK); Tina Spendler, Maaloev (DK); Sven Pedersen, Gentofte (DK); Anders Vikso-Nielsen, Slangerup (DK); Thomas Schafer, Farum (DK); Jiyin Liu, Raleigh, NC (US)

(73) Assignees: Novozymes A/S, Bagsvaerd (DK); Novozymes North America Inc, Franklinton, NC (US)

( * ) Notice: Subject to any disclaimer, the term of this patent is extended or adjusted under 35 U.S.C. 154(b) by 0 days.

(21) Appl. No.: 11/950,856

(22) Filed: Dec. 5, 2007

(65) Prior Publication Data

US 2008/0213862 A1 Sep. 4, 2008

Related U.S. Application Data

(62) Division of application No. 10/877,847, filed on Jun. 25, 2004, now Pat. No. 7,306,935.

(60) Provisional application No. 60/519,554, filed on Nov. 12, 2003, provisional application No. 60/482,589, filed on Jun. 25, 2003, provisional application No. 60/514,854, filed on Oct. 27, 2003.

(30) Foreign Application Priority Data

Jun. 25, 2003 (DK) ............................... 2003 00949
Oct. 24, 2003 (DK) ............................... 2003 01568

(51) Int. Cl.
*C12N 9/28* (2006.01)
*C12N 9/26* (2006.01)
*C12N 9/24* (2006.01)
*C12N 9/00* (2006.01)
*C12P 21/06* (2006.01)
*C12P 19/34* (2006.01)
*C07H 21/04* (2006.01)

(52) U.S. Cl. ...................... 435/202; 435/201; 435/200; 435/183; 435/69.1; 435/91.1

(58) Field of Classification Search ................ 435/202, 435/201, 200, 183, 69.1, 91.1
See application file for complete search history.

(56) References Cited

U.S. PATENT DOCUMENTS

| 4,009,074 A | 2/1977 | Walon |
| 7,407,677 B2 * | 8/2008 | Callen et al. .................. 426/7 |
| 2004/0018607 A1 | 1/2004 | Callen et al. |

FOREIGN PATENT DOCUMENTS

| EP | 0 171 218 | 2/1986 |
| WO | WO 02/068589 | 9/2002 |
| WO | WO02068589 | * 9/2002 |
| WO | WO 2004/091544 | 10/2004 |

OTHER PUBLICATIONS

Seffernick et al., Melamine deaminase and Atrazine chlorohydrolase: 98 percent identical but functionally different. J. Bacteriol.,2001, vol. 183 (8): 2405-2410.*
Witkowski et al., Conversion of b-ketoacyl synthase to a malonyl decarboxylase by replacemnt of the active-site cysteine with glutamine. Biochemistry, 1999, vol. 38: 11643-11650.*
Guo et al., Protein tolerance to random amino acid change. PNAS., 2004, vol. 101 (25): 9205-9210.*
Lin et al., EBI Accession No. Q59222 (1996).
Janecek et al., European Journal of Biochemistry, vol. 270, No. 4, pp. 635-645 (2003).
Southall et al., FEBS Letters, vol. 447, No. 1, pp. 58-60 (1999).
Park et al., Biotechnology and Biogengineering, vol. 24, No. 2, pp. 495-500 (1982).
MacGregor et al., Biochimica et Biophysica Acta, vol. 1546, No. 1, pp. 1-20 (2001).
Igarashi et al., Biochemical and Biophysical Research Communications, vol. 248, pp. 372-377 (1998).
Mielenz, Proc. Natl. Acad Sci. USA, vol. 80, pp. 5975-5979 (1983).
Aiba et al., Applied and Environmental Microbiology, vol. 46, No. 5, pp. 1059-1065 (1983).
Yuuki et al., J. Biochem., vol. 98, No. 5, pp. 1147-1156 (1985).
International Search Report of PCT/US2004/023031 (PCT Counterpart to this application) issued May 24, 2006.

* cited by examiner

*Primary Examiner*—Ganapathirama Raghu
(74) *Attorney, Agent, or Firm*—Elias J. Lambiris

(57) ABSTRACT

The present invention relates to polypeptides having alpha-amylase activity and polynucleotides having a nucleotide sequence which encodes for the polypeptides. The invention also relates to a polypeptide having carbohydrate-binding affinity and polynucleotides having a nucleotide sequence which encodes for the polypeptides. The invention also relates to nucleic acid constructs, vectors, and host cells comprising the nucleic acid constructs as well as methods for producing and using the polypeptides.

17 Claims, 3 Drawing Sheets

POLYPEPTIDES HAVING ALPHA-AMYLASE ACTIVITY AND POLYNUCLEOTIDES ENCODING SAME

CROSS-REFERENCE TO RELATED APPLICATIONS

This application is a divisional of application Ser. No. 10/877,847 filed on Jun. 25, 2004, now U.S. Pat. No. 7,306,935, which claims the benefit of U.S. Provisional application nos. 60/519,554, filed Nov. 12, 2003, 60/482,589, filed Jun. 25, 2003, and 60/514,854, filed Oct. 27, 2003 and priority from Danish application nos. PA 2003 00949, filed Jun. 25, 2003, and PA 2003 01568, filed Oct. 24, 2003, the contents of which are fully incorporated herein by reference.

SEQUENCE LISTING

Applicants enclose a computer readable form of a Sequence Listing.

FIELD OF THE INVENTION

The present invention relates to polypeptides having alpha-amylase activity and polynucleotides having a nucleotide sequence which encodes for the polypeptides. The invention also relates to nucleic acid constructs, vectors, and host cells comprising the nucleic acid constructs as well as methods for producing and using the polypeptides.

BACKGROUND OF THE INVENTION

For a number of years alpha-amylase enzymes have been used for a variety of different purposes, the most important of which are starch liquefaction, textile desizing, starch modification in the paper and pulp industry, and for brewing and baking. A further use of alpha-amylases is removal of starchy stains during washing with a detergent at alkaline pH.

It is an object of the present invention to provide alpha-amylases with a performance suitable for specific applications.

SUMMARY OF THE INVENTION

In a first aspect the present invention relates to a polypeptide having alpha-amylase activity, selected from the group consisting of:
 (a) i) a polypeptide comprising an amino acid sequence which has at least 90% identity with amino acids 1 to 586 of SEQ ID NO:2;
  ii) a polypeptide comprising an amino acid sequence which has at least 96% identity with amino acids 1 to 542 of SEQ ID NO:4;
  iii) a polypeptide comprising an amino acid sequence which has at least 80% identity with amino acids 1 to 583 of SEQ ID NO:6;
 (b) a polypeptide which is encoded by a nucleotide sequence which hybridizes under high stringency conditions with a polynucleotide probe selected from the group consisting of
  (i) the complementary strand of nucleotides 100 to 1857 of SEQ ID NO:1
  (ii) the complementary strand of nucleotides 100 to 1725 of SEQ ID NO:3.
  (iii) the complementary strand of nucleotides 91 to 1839 of SEQ ID NO:5.
 (c) a fragment of (a) or (b) that has alpha-amylase activity.

The invention also relates to a polypeptide having carbohydrate-binding affinity, selected from the group consisting of:
 (a) i) a polypeptide comprising an amino acid sequence which has at least 60% identity with amino acids 485 to 586 of SEQ ID NO:2;
  ii) a polypeptide comprising an amino acid sequence which has at least 60% identity with amino acids 485 to 542 of SEQ ID NO:4:
  iii) a polypeptide comprising an amino acid sequence which has at least 60% identity with amino acids 455 to 583 of SEQ ID NO:6:
 (b) a polypeptide which is encoded by a nucleotide sequence which hybridizes under low stringency conditions with a polynucleotide probe selected from the group consisting of
  (i) the complementary strand of nucleotides 1552 to 1857 of SEQ ID NO:1,
  (ii) the complementary strand of nucleotides 1552 to 1725 of SEQ ID NO:3,
  (iii) the complementary strand of nucleotides 1453 to 1839 of SEQ ID NO:52
 (c) a fragment of (a) or (b) that has carbohydrate binding affinity.

In a second aspect the present invention relates to a polynucleotide sequence having a nucleotide sequence which encodes for the polypeptides of the invention.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a polypeptide of the invention, the method comprising:
 (a) cultivating a strain, which in its wild-type form is capable of producing the polypeptide, to produce the polypeptide; and
 (b) recovering the polypeptide.

In a seventh aspect the present invention relates to a method for producing a polypeptide of the invention, the method comprising:
 (a) cultivating a recombinant host cell of the invention under conditions conducive for production of the polypeptide; and
 (b) recovering the polypeptide.

Other aspects of the present invention will be apparent from the below description and from the appended claims.

DEFINITIONS

Figure 1:
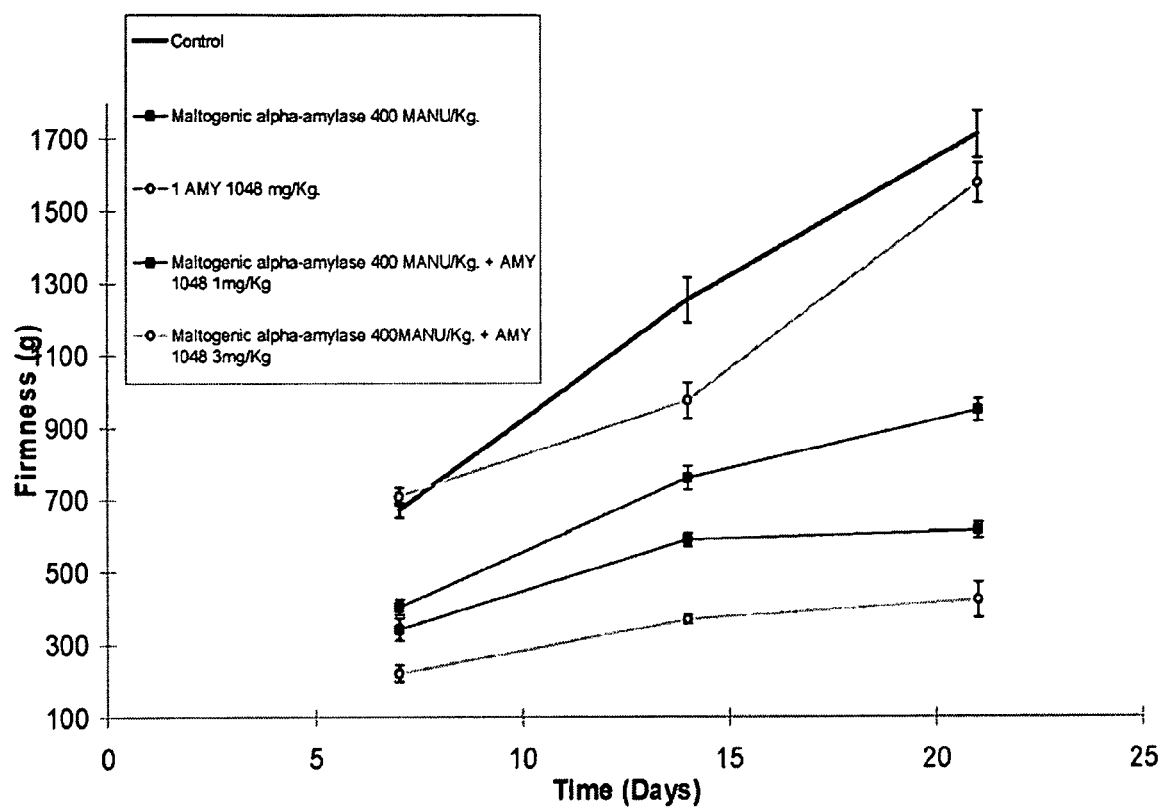
FIG. 1 shows the firmness of bread crumb during 21 days of storage with and without AMY1048 of the invention and/or maltogenic alpha-amylase

Prior to discussing the present invention in further details, the following terms and conventions will first be defined:

Substantially pure polypeptide: In the present context, the term "substantially pure polypeptide" means a polypeptide preparation which contains at the most 10% by weight of other polypeptide material with which it is natively associated (lower percentages of other polypeptide material are preferred, e.g., at the most 8% by weight, at the most 6% by weight, at the most 5% by weight, at the most 4% at the most 3% by weight, at the most 2% by weight, at the most 1% by weight, and at the most 0.5% by weight). Thus, it is preferred that the substantially pure polypeptide is at least 92% pure, i.e., that the polypeptide constitutes at least 92% by eight of the total poly peptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form". i.e., that the polypeptide preparation is essentially free of other polypeptide material with which it is natively associated. This can, be accomplished, for example, by preparing the polypeptide by means of well-known recombinant methods. Herein, the term "substantially pure polypeptide" is synonymous with the terms "isolated polypeptide" and "polypeptide in isolated form".

Alpha-amylase activity: Alpha-amylases (alpha 1,4-alpha-D-glucan glucanohydrolase, EC 3.2.1.1) constitute a group of enzymes, which catalyze hydrolysis of starch and other linear and branched 1,4 glucosidic oligo and polysaccharides. For purposes of the present invention, alpha-amylase activity is determined using the PHADEBAS® assay or the pNPG7 assay described below in the "Materials & Methods"-section.

The polypeptides of the present invention should preferably have at least 20% of the alpha-amylase activity of the polypeptide consisting of the amino acid sequence shown as amino acids in position 1 to 586 of SEQ ID NO:2; or the amino acid sequence shown as amino acids in position 1 to 542 of SEQ ID NO:4; the amino acid sequence shown as amino acids in position or 1 to 583 of SEQ ID No:6, respectively.

In a particular preferred embodiment, the polypeptides should have at least 40%, such as at least 50%, preferably at least 60%, such as at least 70%, more preferably at least 80%, such as at least 90% most preferably at least 95%, such as about or at least 100% of the alpha-amylase activity of the polypeptide consisting of the amino acid sequence shown as amino acids in position 1 to 586 of SEQ ID NO:2; or the amino acid sequence shown as amino acids in position 1 to 542 of SEQ ID NO:4; the amino acid sequence shown as amino acids in position or 1 to 583 of SEQ ID No:6, respectively.

Identity: In the present context, the homology between two amino acid sequences or between two nucleotide sequences is described by the parameter "identity".

For purposes of the present invention, the degree of identity between two amino acid sequences is determined by using the program FASTA included in version 2.0x of the FASTA program package (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA". Methods in Enzymology 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Fragment: When used herein, a "fragment" of SEQ ID NOS:2, 4, and 6, respectively, are polypeptides having one or more amino acids deleted from the amino and/or carboxyl terminus of this amino acid sequence.

Allelic variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g., at the most 8% by weight, at the most 6% by weight, at the most 5% by weight, at the most 4% at the most 3% by weight, at the most 2% by weight, at the most 1% by weight, and at the most 0.5% by weight). A substantially pure polynucleotide may, however, include naturally occurring 5' and 3' untranslated regions, such as promoters and terminators. It is preferred that the substantially pure polynucleotide is at least 92% pure, i.e., that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide," and "polynucleotide in isolated form".

Modification(s): In the context of the present invention the term "modification(s)" is intended to mean any chemicl modification of the polypeptide consisting of the amino acid sequence shown as amino acids in position 1 to 586 or 485 to 586 of SEQ ID NO:2; the amino acid sequence shown as amino acids in position 1 to 542 or 485 to 542 of SEQ ID NO:4, the amino acid sequence shown as amino acids in position 1 to 583 or 455 to 583 of SEQ ID NO:6, respectively, as well as genetic manipulation of the DNA encoding the above mentioned polypeptides. The modification(s) can be replacement(s) of the amino acid side chain(s), substitution(s), deletion(s) and/or insertions(s) in or at the amino acid(s) of interest.

Artificial variant: When used herein, the term "artificial variant" means a polypeptide having alpha-amylase activity and/or carbohydrate-binding affinity, which has been produced by an organism which is expressing a modified gene as compared to SEQ ID NOS: 1, 3, or 5, respectively. The modified gene, from which said variant is produced when expressed in a suitable host, is obtained through human intervention by modification of the nucleotide sequence disclosed in SEQ ID NO: 1, 3 or 5, respectively.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes DNA, cDNA, and recombinant nucleotide sequences.

Expression: In the present context, the term "expression" includes any step involved in the production of the polypeptide including, but not limited to, transcription, post-transcriptional modification, translation, post-translational modification, and secretion.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct.

The terms "polynucleotide probe", "hybridization" as well as the various stringency conditions are defined in the section entitled "Polypeptides Having Alpha-amylase Activity and/or Carbohydrate-Binding Affinity".

The term "binding affinity" means the ability of the domain to bind to a substrate in question, in particular starch. The "binding affinity" may be determined using the method described in the "Materials & Method"-section below.

DETAILED DESCRIPTION OF THE INVENTION

Polypeptides Having Alpha-Amylase Activity and/or Carbohydrate-Binding Affinity

In a first embodiment, the present invention relates to polypeptides having alpha-amylase activity and/or carbohydrate-binding affinity and where the polypeptides comprises, preferably consists of, an amino acid sequence which has a degree of identity to the amino acid sequences shown SEQ ID NOS: 2, 4, 6, respectively.

More specifically, in the first aspect the invention relates to a polypeptide having alpha-amylase activity, selected from the group consisting of:

(a) i) a polypeptide comprising an amino acid sequence which has at least 90% identity with amino acids 1 to 586 of SEQ ID NO:2;
ii) a polypeptide comprising an amino acid sequence which has at least 96% identity with amino acids 1 to 542 of SEQ ID NO:4;
iii) a polypeptide comprising an amino acid sequence which has at least 80% identity with amino acids 1 to 583 of SEQ ID NO:6;

(b) a polypeptide which is encoded by a nucleotide sequence which hybridizes under high stringency conditions with a polynucleotide probe selected from the group consisting of
(i) the complementary strand of nucleotides 100 to 1857 of SEQ ID NO:1,
(ii) the complementary, strand of nucleotides 100 to 1725 of SEQ ID NO:3.
(iii) the complementary strand of nucleotides 91 to 1839 of SEQ ID NO:5, (b) a fragment of (a) or (b) that has alpha-amylase activity, In an embodiment the polypeptide of the invention comprising an amino acid sequence which has at least 90% identity with amino acids 1 to 586 of SEQ ID NO:2, preferably at least 91% identity, preferably at least 92% identity, preferably at least 93% identity, preferably at least 94% identity, preferably at least 95% identity, preferably at least 96% identity, more preferably at least 97% identity, more preferably at least 98% identity, or more preferably at least 99% identity with amino acids 1 to 586 of SEQ ID NO:2.

In another embodiment the polypeptide of the invention comprising an amino acid sequence which has at least 96% identity with amino acids 1 to 542 of SEQ ID NO:4, preferably at least 97% identity, more preferably at least 98% identity, more preferably at least 99% identity with amino acids 1 to 542 of SEQ ID NO:4.

In a further embodiment the polypeptide of the invention comprising an amino acid sequence which has at least 80% identity, with amino acids 1 to 583 of SEQ ID NO:6, preferably at least 85% identity, at least 90% identity, at least 95% identity, preferably at least 96% identity, more preferably at least 97% identity, more preferably at least 98% identity, or more preferably at least 99% identity with amino acids 1 to 583 of SEQ ID NO:6.

In a preferred embodiment polypeptide of the invention comprises either of the amino acids shown in position 1 to 586 of SEQ ID NO:2; or the amino acid sequence shown as amino acids in position 1 to 542 of SEQ ID NO:4; or the amino acid sequence showvn as amino acids in position or 1 to 583 of SEQ ID No:6, respectively.

In another preferred embodiment the polypeptide according to the invention consists of the amino acids 1 to 484 of SEQ ID NO:2; or the amino acids in position 1 to 484 of SEQ ID NO:4; or the amino acids shown in position 1 to 454 of SEQ ID NO:6.

The term "parent polypeptide", "parent protein", "parent enzyme", "standard enzyme", or simply "parent" refers to the polypeptide on which the variant was based. This term also refers to the polypeptide with which a variant is compared and aligned. The parent may be a naturally occurring (wild-type) polypeptide, or it may in turn even be a variant thereof, prepared by any suitable means. For instance, the parent protein may be a variant of a naturally occurring polypeptide which has been modified or altered in the amino acid sequence. A parent may also be an allelic variant which is any of two or more alternative forms of a gene occupying the same chromosomal locus. Allelic variation arises naturally through mutation, and may result in polymorphism within populations as is well-described in the art. An allelic variant of a polypeptide is a polypeptide encoded by the corresponding allelic variant of a gene.

In an embodiment of the invention the polypeptide comprises an amino acid sequence which has at least 90% identity with the polypeptide encoded by the alpha-amylase encoding part of the DNA sequence shown at position 100 to 1857 of SEQ ID NO: 1, preferably at least 91% identity, at least 92% identity, at least 93% identity, at least 94% identity, at least 95% identity, at least 96% identity, at least 97% identity, 98% identity, preferably at least 99% identity with the polypeptide encoded by the alpha-amylase encoding DNA sequence shown at position 100 to 1857 of SEQ ID NO: 1.

In an embodiment the polypeptide of the invention comprises an amino acid sequence which has at least 96% identity with the polypeptide encoded by the alpha-amylase encoding part of the DNA sequence shown at position 100 to 1725 of SEQ ID NO: 3, preferably at least 97% identity, preferably 98% identity, preferably at least 99% identity with the polypeptide encoded by the alpha-amylase encoding part of the DNA sequence shown at position 100 to 1725 of SEQ ID NO: 3.

In an embodiment the polypeptide of the invention comprises an amino acid sequence which has at least 80% identity with the polypeptide encoded by the alpha-amylase encoding part of the DNA sequence shown at position 91 to 1839 of SEQ ID NO: 5, preferably at least 85% identity, preferably at least 90% identity, preferably at least 91% identity preferably at least 91% identity, at least 92% identity, at least 93% identity, at least 94% identity, at least 95% identity, at least 96% identity, at least 97% identity, 98% identity, preferably at least 99% identity with the polypeptide encoded by the alpha-amylase encoding DNA sequence shown at position 91 to 1839 of SEQ ID NO: 5.

In an embodiment the polypeptide of the invention is an artificial variant which comprises an amino acid sequence that has at least one substitution, deletion and/or insertion of an amino acid as compared to the amino acid sequence encoded by the alpha-amylase encoding part of the DNA sequence shown at position 100 to 1857 of SEQ ID NO: 1 or at position 100 to 1725 of SEQ ID NO: 3 or at position 91 to 1839 of SEQ ID NO: 5.

In an interesting embodiment, the amino acid sequence differs by at the most ten amino acids (e.g., by ten amino acids), in particular by at the most five amino acids (e.g., by five amino acids), such as by at the most four amino acids (e.g., by four amino acids), e.g., by at the most three amino acids (e.g., by three amino acids) from amino acids in position 1 to 586 of SEQ ID NO:2; or the amino acid sequence shown as amino acids in position 1 to 542 of SEQ ID NO:4; or the amino acid sequence shown as amino acids in position 1 to 583 of SEQ ID No:6, respectively.

In a particular interesting embodiment, the amino acid sequence differs by at the most two amino acids (e.g., by two amino acids), such as by one amino acid from amino acids in position 1 to 586 of SEQ ID NO: 2; or the amino acid sequence shown as amino acids in position 1 to 542 of SEQ ID NO:4; or the amino acid sequence shown as amino acids in position or 1 to 583 of SEQ ID No:6, respectively.

The polypeptide of the invention may be a wild-type alpha-amylase identified and isolated from a natural source. Such wild-type polypeptides may be specifically screened for by standard techniques known in the art. Furthermore, the polypeptide of the invention malt be prepared by the DNA shuffling technique, such as described in J. E. Ness et al. *Nature Biotechnology* 17, 893-896 (1999). Moreover, the polypeptide of the invention may be an artificial variant which comprises, preferably consists of, an amino acid sequence that has at least one substitution, deletion and/or insertion of an amino acid in position 1 to 586 of SEQ ID NO:2; or the amino acid sequence shown as amino acids in position 1 to 542 of SEQ ID NO:4; or the amino acid sequence shown as amino acids in position or 1 to 583 of SEQ ID No:6, respectively. Such artificial variants may be constructed by standard techniques known in the art, such as by site-directed/random mutagenesis of the polypeptide comprising the amino acid sequence shown as amino acids in position 1 to 586 of SEQ ID NO:2; or the amino acid sequence shown as amino acids in position 1 to 542 of SEQ ID NO:4; or the amino acid sequence shown as amino acids in position or 1 to 583 of SEQ ID No:6, respectively.

In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues, or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, *In the Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

In a third embodiment, the present invention relates to polypeptides having alpha-amylase activity and/or carbohydrate-binding affinity which are encoded by nucleotide sequences which hybridize under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of the complementary strand of nucleotides 100 to 1857 of SEQ ID NO:1, the complementary strand of nucleotides 100 to 1725 of SEQ ID NO:3, the complementary strand of nucleotides 91 to 1839 of SEQ ID NO:5, the complementary strand of nucleotides 100 to 1551 of SEQ ID NO:1, the complementary strand of nucleotides 100 to 1551 of SEQ ID NO:3, the complementary strand of nucleotides 91 to 1452 of SEQ ID NO:5, the complementary strand of nucleotides 1552 to 1857 of SEQ ID NO:1, the complementary strand of nucleotides 1552 to 1725 of SEQ ID NO:3, the complementary strand of nucleotides 1453 to 1839 of SEQ ID NO:5. (J. Sambrook, E.F. Fritsch, and T. Maniatus, 1989, *Molecular Cloning, A Laboratory Manual*, 2d edition, Cold Spring Harbor, N.Y.).

The nucleotide sequence of SEQ ID NOS: 1, 3 or 5, respectively, or a subsequence thereof, as well as the amino acid sequence of SEQ ID NO: 2, 4, or 6, respectively, or a fragment thereof, may be used to design a polynucleotide probe to identify, and clone DNA encoding polypeptides having alpha-amylase activity and/or carbohydrate-binding affinity from strains of different genera or species according to methods well known in the art. In particular, such probes can be used for hybridization with the genomic of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with $^{32}P$, $^{3}H$, $^{35}S$, biotin, or avidin).

Thus, a genomic DNA library prepared from such other organisms may be screened for DNA which hybridizes with the probes described above and which encodes a polypeptide having alpha-amylase activity and/or carbohydrate-binding affinity. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA that is homologous with SEQ ID NOS: 1, 3 or 5, respectively, the carrier material with the immobilized DNA is used in a Southern blot.

For purposes of the present invention, hybridization indicates that the nucleotide sequence hybridizes to a labeled polynucleotide probe which hybridizes to the nucleotide sequence shown in SEQ ID NO: 1, 3 or 5, respectively, under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is selected from the group consisting of the complementary strand of nucleotides 100 to 1857 of SEQ ID NO:1, the complementary strand of nucleotides 100 to 1725 of SEQ ID NO:3, the complementary strand of nucleotides 91 to 1839 of SEQ ID NO:5, the complementary strand of nucleotides 100 to 1551 of SEQ ID NO:1, the complementary strand of nucleotides 100 to 1551 of SEQ ID NO:3, the complementary strand of nucleotides 91 to 1452 of SEQ ID NO:5, the complementary strand of nucleotides 1552 to 1857 of SEQ ID NO:1, the complementary strand of nucleotides 1552 to 1725 of SEQ ID NO:3, the complementary strand of nucleotides 1453 to 1839 of SEQ ID NO:5, respectively.

For long probes of at least 100 nucleotides in length, very low to very high stringency conditions are defined as prehybridization and hybridization at 42° C. in 5×SSPE, 1.0% SDS, 5×Denhardt's solution, 100 micro g/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g., probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

Sources for Polypeptides Having Alpha-Amylase Activity and/or Carbohydrate-Binding Affinity A polypeptide of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted. In a preferred embodiment, the polypeptide is secreted extra-cellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus flavothermus, Bacillus lautus, Bacillus lentis, Bacillus licheniformis, Bacillus megaterium, Bacillus stearothermophilus, Bacillus subtilis,* or *Bacillus thuringiensis* polypeptide; or a Streplomyces polypeptide, e.g., a *Streptomyces lividans* or *Streptomyces murinus* polypeptide; or a gram negative bacterial polypeptide, e.g., an *E. coli* or a *Pseudomonas* sp. polypeptide.

In a more preferred embodiment, the polypeptide is a *Bacillus* sp. polypeptide. It will be understood that for the aforementioned species, the invention encompasses both the perfect and imperfect states, and other taxonomic equivalents, e.g. anamorphs, regardless of the species name by which they are known. Those skilled in the art will readily recognize the identity of appropriate equivalents.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g. Sambrook et al., 1989, Molecular Cloning: A Laboratory Manual, 2nd Ed., Cold Spring Harbor, 1989).

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. In a preferred embodiment the nucleotide sequence is set forth in SEQ ID NO: 1, 3, or 5, respectively. In a more preferred embodiment, the nucleotide sequence is the mature polypeptide coding region of SEQ ID NO: 1, 3, or 5, respectively.

The present invention also encompasses polynucleotides having, preferably consisting of, nucleotide sequences which encode a polypeptide consisting of the amino acid sequence of SEQ ID NO: 2, 4 or 6, respectively, or the mature polypeptide thereof, which differ from SEQ ID NO: 1, 3 or 5, respectively, by virtue of the degeneracy of the genetic code.

The present invention also relates to polynucleotides having, preferably consisting of a subsequence of SEQ ID NO: 1, 3, or 5, respectively, which encode fragments of SEQ ID NO: 2, 4 or 6, respectively, that has alpha-amylase activity and/or carbohydrate-binding activity. A subsequence of SEQ ID NO: 1, 3 or 5, respectively, is a nucleotide sequence encompassed by SEQ ID NO: 1, 3 or 5, respectively, except that one or more nucleotides from the 5' and/or 3' end have been deleted.

The present invention also relates to polynucleotides having, preferably consisting of, a modified nucleotide sequence which comprises at least one modification in the mature polypeptide coding sequence of SEQ ID NO: 1, 3 or 5, respectively, and where the modified nucleotide sequence encodes a polypeptide which consists of amino acids in position 1 to 586 of SEQ ID NO:2; or the amino acid sequence shown as amino acids in position 1 to 542 of SEQ ID NO:4 or the amino acid sequence shown as amino acids in position or 1 to 583 of SEQ ID No:6, respectively.

The techniques used to isolate or clone a nucleotide sequence encoding a polypeptide are known in the art and include isolation from genomic DNA, preparation from cDNA, or a combination thereof. This will be described further below.

DNA Encoding an Alpha-amylase of the Invention

The present invention also relates to a polynucleotide having, preferably consisting of, a nucleotide sequence which has at least 60% identity with nucleotides selected from the group consisting of nucleotides 100 to 1857 of SEQ ID NO:1, nucleotides 100 to 1725 of SEQ ID NO:3, nucleotides 91 to 1839 of SEQ ID NO:5, nucleotides 100 to 1551 of SEQ ID NO:1, nucleotides 100 to 1551 of SEQ ID NO:3, nucleotides 91 to 1452 of SEQ ID NO:5, nucleotides 1552 to 1857 of SEQ ID NO:1, nucleotides 1552 to 1725 of SEQ ID NO:3, nucleotides 1453 to 1839 of SEQ ID NO:5.

Preferably, the nucleotide sequence has at least 70% identity, e.g., at least 80% identity, such as at least 90% identity, more preferably at least 95% identity, such as at least 96% identity, e.g. at least 97% identity, even more preferably at least 98% identity, such as at least 99% with any of the nucleotides in SEQ ID NO: 1, 3 or 5, respectively, mentioned right above. Preferably, the nucleotide sequence encodes a polypeptide having alpha-amylase activity and/or carbohydrate-binding affinity. The degree of identity between two nucleotide sequences is determined as described previously (see the section entitled "Definitions"). Preferably, the nucleotide sequence comprises nucleotides 100 to 1857 of SEQ ID NO:1, nucleotides 100 to 1725of SEQ ID NO:3, nucleotides 91 to 1839 of SEQ ID NO:5, nucleotides 100 to 1551 of SEQ ID NO:1, nucleotides 100 to 1551 of SEQ ID NO:3, nucleotides 91 to 1452 of SEQ ID NO:5, nucleotides 1552 to 1857 of SEQ ID NO:1, nucleotides 1552 to 1725 of SEQ ID NO:3, nucleotides 1453 to 1839 of SEQ ID NO:5.

In an even more preferred embodiment, the nucleotide sequence consists of nucleotides 100 to 1857 of SEQ ID NO:1, nucleotides 100 to 1725 of SEQ ID NO:3, nucleotides 91 to 1839 of SEQ ID NO:5, nucleotides 100 to 1551 of SEQ ID NO:1, nucleotides 100 to 1551 of SQ ID NO:3, nucleotides 91 to 1452 of SEQ ID NO:5, nucleotides 1552 to 1857 of SEQ ID NO:1, nucleotides 1552 to 1725 of SEQ ID NO:3, nucleotides 1453 to 1839 of SEQ ID NO:5.

Modification of a nucleotide sequence encoding a polypeptide of the present invention may be necessary for the synthesis of a polypeptide, which comprises an amino acid sequence that has at least one substitution, deletion and/or insertion as compared to amino acids in position 1 to 586 of SEQ ID NO:2; or the amino acid sequence shown as amino acids in position 1 to 542 of SEQ ID NO:4; or the amino acid sequence shown as amino acids in position or 1 to 583 of SEQ ID No:6, respectively.

These artificial variants may differ in some engineered way from the polypeptide isolated from its native source, e.g. variants that differ in specific activity the thermostability, pH optimum, or the like.

It will be apparent to those skilled in the art that such modifications can be made outside die regions critical to the function of the molecule and still result in an active polypeptide. Amino acid residues essential to the activity of the polypeptide encoded by the nucleotide sequence of the invention, and therefore preferably not subject to modification, such as substitution, may, be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for alpha-amylase activity and/or carbohydrate-binding affinity to identify, amino acid residues that are critical to the activity or affinity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Moleculor Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods knowvn in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al, 1991, *Protein Expression and Purification* 2: 95-107.

The present invention also relates to a polynucleotide having, preferably consisting of, a nucleotide sequence which encodes a polypeptide having alpha-amylase activity and/or carbohydrate-binding activity, and which hybridizes under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of the complementary strand of nucleotides 100 to 1857 of SEQ ID NO:1, the complementary strand of nucleotides 100 to 1725 of SEQ ID NO:3, the complementary strand of nucleotides 91 to 1839 of SEQ ID NO:5, the complementary strand of nucleotides 100 to 1551 of SEQ ID NO:1, the complementary strand of nucleotides 100 to 1551 of SEQ ID NO:3, the complementary strand of nucleotides 91 to 1452 of SEQ ID NO:5, the complementary strand of nucleotides 1552 to 1857 of SEQ ID NO:1, the complementary strand of nucleotides 1552 to 1725 of SEQ ID NO:3, the complementary strand of nucleotides 1453 to 1839 of SEQ ID NO:5, respectively.

As will be understood, details and particulars concerning hybridization of the nucleotide sequences will be the same or analogous to the hybridization aspects discussed in the section entitled "Polypeptides Having Alpha-Amylase Activity and/or Carbohydrate-Binding Activity" herein.

Cloning a DNA Sequence Encoding an Alpha-amylase of the Invention

The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain of *Bacillus*, or another or related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof A genomic DNA and/or cDNA library may be constructed using chromosomal DNA or messenger RNA from the organism that produces an alpha-amylase. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., die phosphoroamidite method described by S. L. Beaucage and M. H. Caruthers, *Tetrahedron Letters* 2, 1981, pp. 1859-1869, or the method described by Matthes et al., *The EMBO J.* 3, 1984, pp. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487-491.

Expression of Alpha-amylase

According to the invention, a DNA sequence encoding the alpha-amylase produced as described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

Control Sequence

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyvQ), *Bacillus licheniformis* penicillinase gene (perP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, Molecular Cloning: A Laboratory Manual, 2nd Ed., Cold Spring Harbor, 1989.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GALI), *Saccharomyces cerevisiae* alcohol dehydrogenase/glyceraldelyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Terminators

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, *Yeast* 8: 423-488.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Leader Sequence

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1). *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Polyadenylation Sequences

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biologic* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

The signal peptide coding region may be nucleotides 1 to 99 of SEQ ID NO:1 which encode amino acids −33 to −1 of SEQ ID NO:2. The signal peptide coding region may be nucleotides 1 to 99 of SEQ ID NO:3 which encode amino acids −33 to −1 of SEQ ID NO:4. The signal peptide coding region may be nucleotides 1 to 90 of SEQ ID NO:5, which encode amino acids −30 to −1 of SEQ ID NO:6.

Signal Peptide

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simionen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, *Yeast* 8: 423-488.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Expression Vectors

The present invention also relates to recombinant expression vectors comprising the nucleic acid construct of the invention. The various nucleotide and control sequences described above may be joined together to produce a recombinant expression vector which may, include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Selectable Markers

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2. HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate syrnthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

Origins of Replication

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional cop), of the sequence into the host cell genome or by including an amplifiable selectable marker gene With the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, Molecular Cloning: A Laboratory Manual, 2nd Ed., Cold Spring Harbor, 1989).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism: e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilis*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dowver, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In an embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R, eds, *Soc. App. Bacteriol. Symposium Series No.* 9, 1980).

Examples of preferred yeast host cells include *Candida, Hansenula, Kluyveromyces, Pichia, Saccharomyces, Schizosaccharomyces*, or *Yarrowia* cell.

In a most preferred embodiment, the y east host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

A preferred filamentous fungal host cell includes a cell of a species of, but not limited to, *Acremonium, Aspergillus, Fusarium, Humicola, Mucor, Myceliophthora, Neurospora, Penicillium, Thielavia, Tolypocladiurm,* or *Trichodernia.*

In a most preferred embodiment, the filamentous fungal host cell is an *Aspergillus awamori, Aspergillus foetidtis, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusariurm culmorum, Fusarium gramineanum, Fusarium graminum, Fusarium heterosporum, Fusarium negundi, Fusarium oxysporum, Fusarium reliculatum, Fusarium roseum, Fusarium sambucinum, Fusarium sarcochroum, Fusarium sporotrichioides, Futsarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichodernia harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787. Yeast may be transformed using the procedures described by Becker and Guarcnte, In Abelson, J. N. and Simon, M. I., editors, *Guide to Yeast Genetics and Molecular Biology Melhods in Enzymology*, Volume 194, pp 182-187, Academic Press. Inc., New York; Ito et al. 1983, *Journal of Bacteriology* 153: 163; and Hinnen et at. 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably the strain is of the genus *Bacillts*, and more preferably *Bacillus* sp.

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

INDUSTRIAL APPLICATIONS

An alpha-amylase of the invention is well suited for use in a variety of industrial processes, in particular die enzyme finds potential applications as a component in detergents, e.g., laundry, dishwashing and hard surface cleaning detergent compositions, but is also useful for desizing of textiles, fabrics and garments, beer making or brewing, bread making, in pulp and paper production, and further in the production of sweeteners and ethanol and other fermentation products, especially fuel, drinking and industrial ethanol from, e.g., starch or whole grains.

Starch Conversion

Conventional starch-conversion processes, such as liquefaction and saccharification processes, are described, e.g., in U.S. Pat. No. 3,912,590 and EP patent publications Nos. 252,730 and 63,909, hereby incorporated by reference.

Production of Fermentation Product

A fermentation product, especially ethanol, may be produced using any methods know in the art. One example of producing ethanol, wherein an alpha-amylase of the invention may be used is disclosed in U.S. Pat. No. 5,231,017 which is hereby incorporated by reference.

Further, a process wherein an alpha-amylase of the invention may be used is disclosed in DK patent applications PA 2003 00949 and PA 2003 01568 (hereby incorporated by reference). Said process is for hydrolysing granular starch into a soluble starch hydrolysate at a temperature below the initial gelatinization temperature of said granular starch.

Pulp and Paper Production

The alpha-amylase of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

An alpha-amylase of the invention may also be very useful in modifying starch where enzymatically modified starch is used in papermaking together with alkaline fillers such as calcium carbonate, kaolin and clays. With an alpha-amylases of the invention it becomes possible to modify the starch in the presence of the filler thus allowing for a simpler integrated process.

Desizing of Textiles, Fabrics and Garments

An alpha-amylase of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which die fabric is scoured, bleached and dyed. Enzymatic starch breakdown is preferred because it does not involve any handful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporate by reference. Thus, in an embodiment the invention relates to a process for desizing a sized textile, fabric or garment containing starch or starch derivatives, which process comprises treating the fabric with an alpha-amylase of the invention.

Beer Making

The alpha-amylases of the invention may also be very useful in a beer-making process; the alpha-amylases will typically be added during the mashing process.

Detergent Compositions

An alpha-amylase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising die enzyme of the invention. The detergent additive as well as the detergent composition may comprise one or more other enzymes such as a protease, a lipase, a cutinase, an amylase, a carbohydrase, a cellulase, a pectinase, such as pectate lyase; a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. In a preferred embodiment the protease is derived from strain of *Bacillus* sp. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g. subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or mole of the following positions: 27, 36, 57, 76, 87, 97, 101, 104, 120, 123, 167, 170, 194, 206, 218, 222, 224, 235 and 274.

Preferred commercially available protease enzymes include ALCALASE™, SAVINASE™, PRIMASE™, DURALASE™, ESPERASE™, EVERLASE™ and KANNASE™ (Novozymes A/S, Denmark), MAXATASE™, MAXACAL™, MAXAPEM™, PROPERASE™, PURAFECT™, PURAFECT OXP™, FN2™, AND FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudornonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94101541, EP 407 225, EP 260 105, WO 95/35381, WO 96/00292. WO 95/30744, WO 94/25578, WO 95/14783, WO 95/22615, WO 97/04079 and WO 97/07202.

Preferred commercially available lipase enzymes include LIPOLASE™ and LIPOLASE™ ULTRA (Novozymes A/S, Denmark).

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839.

Examples of useful amylases are the variants described in WO 94/02597. WO 94/18314. WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, STAINZYME™, NATALASE™, TERMAMYL™, FUNGAMYL™ and BAN™ (Novozyme A/S, Denmark), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus, Pseiedomonas, Humicola. Fusarium, Thielavia, Acremonium*, e.g. the fungal cellulases produced from *Humicola insolens, Myceliophthora thermophila* and *Fusarium oxysporum* disclosed in U.S. Pat. No. 4,435,307. U.S. Pat. No. 5,648,263, U.S. Pat. No. 5,691,178: U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940, WO 02/099091. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544.

Commercially available cellulases include CELLUZYME™, CAREZYME™, RENOZYME™ (Novozymes A/S, Denmark), CLAZINASE™, and PURADAX HA™ (Genencor International Inc.), and KAC-500(B)™ (Kao Corporation).

Mannanases: Any mannanase suitable for use in alkaline solutions can be used. Suitable mannanases include those of bacterial or fungal origin. Chemically or genetically modified mutants are included.

In a preferred embodiment the mannanase is derived from a strain of the genus *Bacillus*, especially *Bacillus* sp. 1633 disclosed in positions 31-330 of SEQ ID NO:2 or in SEQ ID NO: 5 of WO 99/64619 or *Bacillus agaradhaerens*, for example from the type strain DSM 8721.

Commercially Available Maninanases Include MANNAWAY™ (Novozymes A/S)

Pectate Iyase: Any pectate lyase suitable for use in alkaline solutions can be used. Suitable pectate lyases include those of bacterial or fungal origin. Chemically or genetically modified mutants are included.

In a preferred embodiment the pectate Iyase is derived from a strain of the genus *Bacillus*, especially a strain of *Bacillus substilis*, especially *Bacillus subtilis* DSM14218 disclosed in SEQ ID NO:2 or a variant thereof disclosed in Example 6 of WO 02/092741 or *Bacillus licheniformis*, preferably the *Bacilltus licheniformis* disclosed in U.S. Pat. No. 6,284,524.

Commercially Available Pectate Lyases Include PECTAWAY™ (Novozymes A/S)

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S, Denmark). The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine "glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Dishwash

Example of a dishwash composition of the invention comprising an alpha-amylase of the invention and preferably at least a protease, especially a *Bacillus* protease, such as SAVINASE™, can be found below.

1) Powder Automatic Dishwashing Composition

| | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2) Powder Automatic Dishwashing Composition

| | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

3) Powder Automatic Dishwashing Composition

| | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4) Powder Automatic Dishwashing Composition

| | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5) Powder Automatic Dishwashing Composition

| | |
|---|---|
| Nonionic surfactant | 1-7% |
| Sodium disilicate | 18-30% |
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

6) Powder and Liquid Dishwashing Composition with Cleaning Surfactant System

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |

-continued

| | |
|---|---|
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

7) Non-Aqueous Liquid Automatic Dishwashing Composition

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8) Non-Aqueous Liquid Dishwashing Composition

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) Liquid Automatic Dishwashing Composition

| | |
|---|---|
| Alcohol ethoxylate | 0-20% |
| Fatty acid ester sulphonate | 0-30% |
| Sodium dodecyl sulphate | 0-20% |

-continued

| | |
|---|---|
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) Liquid Automatic Dishwashing Composition Containing Protected Bleach Particles

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1). 2): 3), 4), 6) and 10), wherein perborate is replaced by percarbonate.

12) Automatic dishwashing compositions as described in 1)-6) which additionally contain a manganese catalyst. The manganese catalyst may, e.g., be one of the compounds described in "Efficient manganese catalysts for low-temperature bleaching". *Nature* 369, 1994, pp. 637-639.

Dough-Based Products

An alpha-amylase of the invention may be used for the preparation of a dough-based edible product. In a preferred embodiment an alpha-amylase of the invention is added in an amount of 0.01 to 10 mg/kg flour, preferably 0.5 to 5 mg/kg flour, especially 0.1 to 3 mg/kg flour. The dough generally comprises flour (particularly wheat flour) and water. The dough is leavened, e.g., by adding chemical leavening agents or yeast, usually *Saccharomyces cerevisiae* (baker's yeast).

The dough-based product is made by leavening and heating the dough, e.g., by baking or steaming. Examples are steamed or baked bread (in particular white, whole-meal or rye bread), typically in the form of loaves or rolls.

The dough may comprise one or more additional enzymes, e.g., a second amylase (e.g., a maltogenic alpha-amylase), a cyclodextrin glucanotransferase, a protease or peptidase, in particular an exopeptidase, a transglutaminase, a lipase, a phospholipase, a cellulase, a hemicellulase (e.g., a pentopsanase or xylanase), a glycosyltransferase, a branching enzyme (1,4-alpha-glucan branching enzyme) or an oxidase such as glucose oxidase or an oxidase with higher activity on maltose than on glucose.

Dough

The dough is leavened, e.g., by adding chemical leavening agents or yeast, usually *Saccharomyces cerevisiae* (baker's yeast).

The dough generally comprises meal, flour or starch such as wheat meal, wheat flour, corn flour, corn starch, rye meal, rye flour, oat flour, oat meal, sorghum meal, sorghum flour, rice flour, potato meal, potato flour or potato starch.

The dough may be fresh, frozen or par-baked.

The dough may be a laminated dough.

The dough may also comprise other conventional dough ingredients, e.g.: proteins, such as milk powder and gluten; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate. The dough may comprise fat (triglyceride) such as granulated fat or shortening.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

Edible Product

The process of the invention is used for preparing an edible product by leavening the dough and heating it, e.g., by baking or steaming. The product may be of a soft or a crisp character, either of a white, light or dark type. Examples are steamed or baked bread (in particular white, whole-meal or rye bread), typically in the form of loaves or rolls, French baguette-type bread, pita bread, tortillas, cakes, pancakes, biscuits, cookies, pie crusts, crisp bread, steamed bread, pizza and the like.

Optional Additional Enzyme

An alpha-amylase of the invention may optionally be used together with one or more additional enzymes.

The additional enzyme may be a lipolytic enzyme, particularly phospholipase, galactoilipase and/or triacyl glycerol lipase activity, e.g., as described in WO 9953769, WO 0032758. WO 0200852 or WO 2002066622.

Further, the additional enzyme may be a second amylase, a cyclodextrin glucanotransferase, a protease or peptidase, in particular an exopeptidase, a transglutaminase, a lipase, a phospholipase, a cellulase, a hemicellulase, a glycosyltransferase, a branching enzyme (1,4-alpha-glucan branching enzyme) or an oxidoreductase. The additional enzyme may be of mammalian, plant or microbial (bacterial, yeast or fungal) origin.

The second amylase may be from a fungus, bacterium or plant. It may be a maltogenic alpha-amylase (EC 3.2.1.133), e.g. from *B. stearothermophilus*, an alpha-amylase, e.g. from *Bacillus*, particularly *B. licheniformis* or *B. amyloliquefaciens*, a beta-amylase, e.g. from plant (e.g. soy bean) or from microbial sources (e.g. *Bacillus*), a glucoamylase, e.g. from *A. niger*, or a fungal alpha-amylase, e.g. from *A. oryzae*.

The hemicellulase may be a pentosanase, e.g. a xylanase which may be of microbial origin, e.g. derived from a bacterium or fungus, such as a strain of *Aspergillus*, in particular of *A. aculeatus, A. niger, A. awamori*, or *A. tubigensis*, from a strain of *Trichoderma*, e.g., *T. reesei*, or from a strain of *Humicola*, e.g., *H. insolens*, or from *Bacillus*, e.g., *B. subtilis*.

The protease may be from *Bacillus*, e.g. *B. amyloliquefaciens*.

The oxidoreductase may be a glucose oxidase, a hexose oxidase, a lipoxidase, a peroxidase, or a laccase.

Dough and/or Bread-improving Additive

An alpha-amylase of the invention may be provided as a dough and/or bread improving additive in the form of a granulate or agglomerated powder. The dough and/or bread improving additive preferably may particularly have a narrow particle size distribution with more than 95% (by weight) of the particles in the range from 25 to 500 μm.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Composition Comprising an Alpha-amylase of the Invention

The present invention is further described by the following examples which should not be construed as limiting the scope of the invention.

In an aspect, the invention relates to a composition comprising an alpha-amylase of the invention. In an embodiment the composition of the invention additionally comprises one or more enzymes selected from the group consisting of a cellulase, such as an endoglucanase, a lipase, a cutinase, an oxidoreductase, a protease, another amylase, a hemicellulase, such as a mannanase, a xylanase, a galactanase, an arabinofuranosidase, an esterase, a lichenase, an arabinanases, a pectate lyase, and a mixture thereof. Specific enzyme may be any of the above mentioned.

Use of an Alpha-amylase of the Invention

Finally, the invention also relates to the use of an alpha-amylase of the invention. In preferred embodiment the invention relates to the use of an alpha-amylase of the invention or composition of the invention for treating textiles, fabrics, yarn, or garments, especially for desizing textiles, fabrics, yarn, or garments. An alpha-amylase of the invention may also be used in dough, such as for improving the elasticity of bread crumb of a baking product or for improving the firmness of bread crumb of a baking product or for improving the softness of bread crumb of a baking product or for improving the moistness of a baking product. An alpha-amylase of the invention may also be used in a detergent composition; in particular a laundry detergent composition and a dish wash detergent composition.

An alpha-amylase of the invention may also be used for liquefaction of starch or in an ethanol production process.

Material and Methods:

Chemicals used as buffers and substrates were commercial products of at least reagent grade.

Materials:

Enzymes:

Maltogenic alpha-amylase derived from *B. stearothermophilus* strain NCIB 11837 described in EP 120,693 (available from Novozymes A/S, Denmark).

Xylanase II derived from *Aspergillus aculeatus* CBS 101.43 disclosed as Xyl II in WO 94/21785 (available from Novozymes A/S. Denmark).

Ingredients:

Emulsifier: SSL—sodium stearoyl-2-lactulate-Palsgaard 3426

Dough strengthener: ADA—Azodicarbonamide—SIGMA

General Molecular Biology Methods:

Unless otherwise mentioned the DNA manipulations and transformations were performed using standard methods of molecular biology (Sambrook et al. (1989) Molecular Cloning: A Laboratory Manual, 2nd Ed. Cold Spring Harbor, 1989; Ausubel et al. (1995); Harwood and Cutting (1990).

Fermentation of Alpha-amylases

Fermentation may be performed by methods well known in the art or as follows.

A *B. subtilis* strain harboring the relevant expression plasmid is streaked on a LB-agar plate with 10 micro g/ml Kanamycin from −80° C. stock, and grown overnight at 37° C.

The colonies are transferred to 100 ml BPX media supplemented with 10 micro g/ml kanamycin in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| Na$_2$HPO$_4$, 12 H$_2$O | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris. pH 9.0 and applied on a Q-sepharose F.F. and eluted with a linear gradient from 0-0.3M NaCl over 6 column volumes. The fractions, which contain the activity (measured by the Phadebas assay) are pooled, pH was adjusted to pH 7.5 and remaining color was removed by a treatment with 0.5% W/vol, active coal in 5 minutes.

Determination of Alpha-amylase Activity

1. PHADEBAS® Assay

Alpha-amylase activity is determined by a method employing PHADEBAS® tablets as substrate. PHADEBAS tablets (PHADEBAS® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM CaCl$_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method (PNP-G7 Assay)

Alpha-amylase activity is determined by a method employing the PNP-G7 substrate. PNP-G7 which is a abbreviation for p-nitrophenyl-alpha D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at lambda=405 nm. (400-420 nm.). Kits containing PNP-G7 substrate and alpha-Glucosidase is manufactured by Boehringer-Mannheim (cat.No. 1054635).

To prepare the substrate one bottle of substrate (BM 1442309) is added to 5 ml buffer (BM1442309). To prepare the alpha-Glucosidase one bottle of alpha-Glucosidase (BM 1462309) is added to 45 ml buffer (BM1442309). The working solution is made by mixing 5 ml alpha-Glucosidase solution with 0.5 ml substrate.

The assay is performed by transforming 20 micro 1 enzyme solution to a 96 well microtitre plate and incubating at 25° C. 200 micro 1 working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question tinder the given set of conditions.

Determination of Cutinase Activity (LU)

The cutinase activity is determined as lipolytic activity determined using tributyrine as substrate. This method was based on the hydrolysis of tributyrin by the enzyme, and the alkali consumption is registered as a function of time. One Lipase Unit (LU) is defined as the amount of enzyme which, under standard conditions (i.e. at 30° C.; pH 7; with Gum Arabic as emulsifier and tributyrine as substrate) liberates 1 micro mol titrable butyric acid per minute. A folder AF 95/5 describing this analytical method in more detail is available upon request from Novozymes A/S. Denmark, which folder is hereby included by reference.

Determination of Xylanolytic Activity (FXU)

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue color in the supernatant (as determined spectrophotometrically at 585 nm) is proportional to the xylanase activity, and the xylanase units are then determined relatively to an enzyme standard at standard reaction conditions. i.e. at 50.0° C., pH 6.0, and 30 minutes reaction time.

A folder EB-SM-352.02/01 describing this analytical method in more detail is available upon request to Novozymes A/S, Denmark, which folder is hereby included by reference.

Determination of Cellulytic Activity (EGU)

The cellulytic activity may be measured in endo-glucanase units (EGU), determined at pH 6.0 with carboxymethyl cellulose (CMC) as substrate. A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g., MIVI 3000 from Sofraser, France), thermostated at 40° C. for 30 minutes. One EGU is defined as the amount of enzyme that reduces the viscosity to one half under these conditions. The amount of enzyme sample should be adjusted to provide 0.01-0.02 EGU/ml in the reaction mixture. The arch standard is defined as 880 EGU/g.

A folder EB-SM-0275.02/01 describing this analytical method in more detail is available upon request to Novozymes A/S, Denmark, which folder is hereby included by reference.

Determination of Maltogenic Amylase Activity (MANU)

One MANU (Maltogenic Amylase Novo Unit) may be defined as the amount of enzyme required to re-lease one mol of maltose per minute at a concentration of 10 mg of maltotriose (Sigma M 8378) substrate per ml of 0.1 M citrate buffer, pH 5.0 at 37 C. for 30 minutes:

Sponge & Dough-Method

Sponge and Dough Procedure:

| Recipe | |
|---|---|
| | % on flour basis |
| Sponge | |
| Soya oil | 2.5 |
| Sodium Stearoyl-2-lactulate | 0.38 |
| Yeast | 5 |
| Wheat flour | 60 |
| Water | 62 |
| Dough | |
| Ascorbic acid | to be optimized for each flour |
| Azodicarbonamide | 20 ppm |
| Salt | 2 |
| Syrup | 7 (dry substance) |
| Water | to be optimized for each flour |
| Wheat flour | 40 |
| Calcium propionate + enzymes | 0.25 |

Sponge

Scaling of ingredients, addition of yeast, water, flour, SSL and oil into mixer bowl. Mixing at 90 rpm for 1 minute, 150 rpm for 4 minutes. The sponge is weighted, the temperature is measured and the sponge is placed in a bowl ~fermentation 3 hours at 27° C., 86% RH.

Dough

Addition of ingredients and the sponge into the mixer bowl. The sponge and ingredients are mixed together 90 rpm for 9 minutes. The temperature is measured, dough characteristics are evaluated; the dough is scaled into small pieces of 435 g each. The dough rests on the table for 10 minutes. Dough is sheeted and molded. Fermentation for 55 minutes at 42° C. and 86% RH. Bread is baked at 200° C. for 22 minutes.

Affinity of Bindings Domain

Adsorption of starch binding domain (SBD) onto granular starch is determined by incubating increasing amounts of SBD (0-3 mg/ml) with granular corn starch (10 mg/ml) in 5 mM sodium acetate, pH 3.6 at 4° C. for 16 hours, essentially as described (Belshaw. & Williamson, FEBS Lett. 1990 Sep. 3; 269(2):350-3). The reaction is terminated by centrifugation and the protein concentration in the supernatant is subsequently determined and subtracted from the total protein to give the amount of starch bound protein.

General Method For Random Mutagenesis By Use of the DOPE Program

The random mutagenesis may be carried out by the following steps:

1. Select regions of interest for modification in the parent enzyme,
2. Decide on mutation sites and non-mutated sites in the selected region,
3. Decide on which kind of mutations should be carried out, e.g., with respect to the desired stability and/or performance of the variant to be constructed,
4. Select structurally reasonable mutations,
5. Adjust the residues selected by step 3 with regard to step 4.
6. Analyze by use of a suitable dope algorithm the nucleotide distribution.
7. If necessary, adjust the wanted residues to genetic code realism, e.g., taking into account constraints resulting from the genetic code, e.g., in order to avoid introduction of stop codons; the skilled person will be aware that some codon combinations cannot be used in practice and will need to be adapted
8. Make primers
9. Perform random mutagenesis by use of the primers
10. Select resulting alpha-amylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

Filter Screening Assays

The assay can be used to screening of variants having an improved stability, at high pH compared to the parent enzyme and alpha-amylase variants having an improved stability at high pH and medium temperatures compared to die parent enzyme depending of die screening temperature setting High pH Filter Assay

*Bacillus* libraries are plated on a sandwich of cellulose acetate (OE 67. Schleicher & Schuell, Dassel, Germany)— and nitrocellulose filters (Protran-Ba 85, Schleicher & Schuell, Dassel, Germany) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10°-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours, at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Low Calcium Filter Assay

The *Bacillus* library are plated on a sandwich of cellulose acetate (OE 67, Schleicher & Schuell, Dassel, Germany)— and nitrocellulose filters (Protran-Ba 85, Schleicher & Schuell, Dassel, Germany) on TY agar plates with a relevant antibiotic, e.g. kanamycin or chlormphenicol, at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants

|  | 1 | 2 | 3 | 4 | 5 |
|---|---|---|---|---|---|
| Maltogenic alpha-amylase MANU/kg | 0 | 400 | — | 400 | 400 |
| AMY 1048 mg/kg | 0 | — | 1 | 1 | 3 |
| XYL II FXU/kg | 0 | — | — | — | — | is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours, at room temperature. After removal of the filters the assay plates are stained with 10% Lugol® solution. Starch degrading variants are detected as white spots on dark blue background and then identified on the storage plates. Positive variants are re-screened twice under the same conditions as the first screen.

EXAMPLES

Example 1

Softness and Moistness of Bread Crumb Using AMY1048

Bread was baked according to the "Sponge & Dough"-method described in the "MATERIALS & METHODS" section. Enzymes were dosed according to the table below:

Table 1: Enzyme Dosages

The bread was stored at room temperature until analysis

Figure 2:
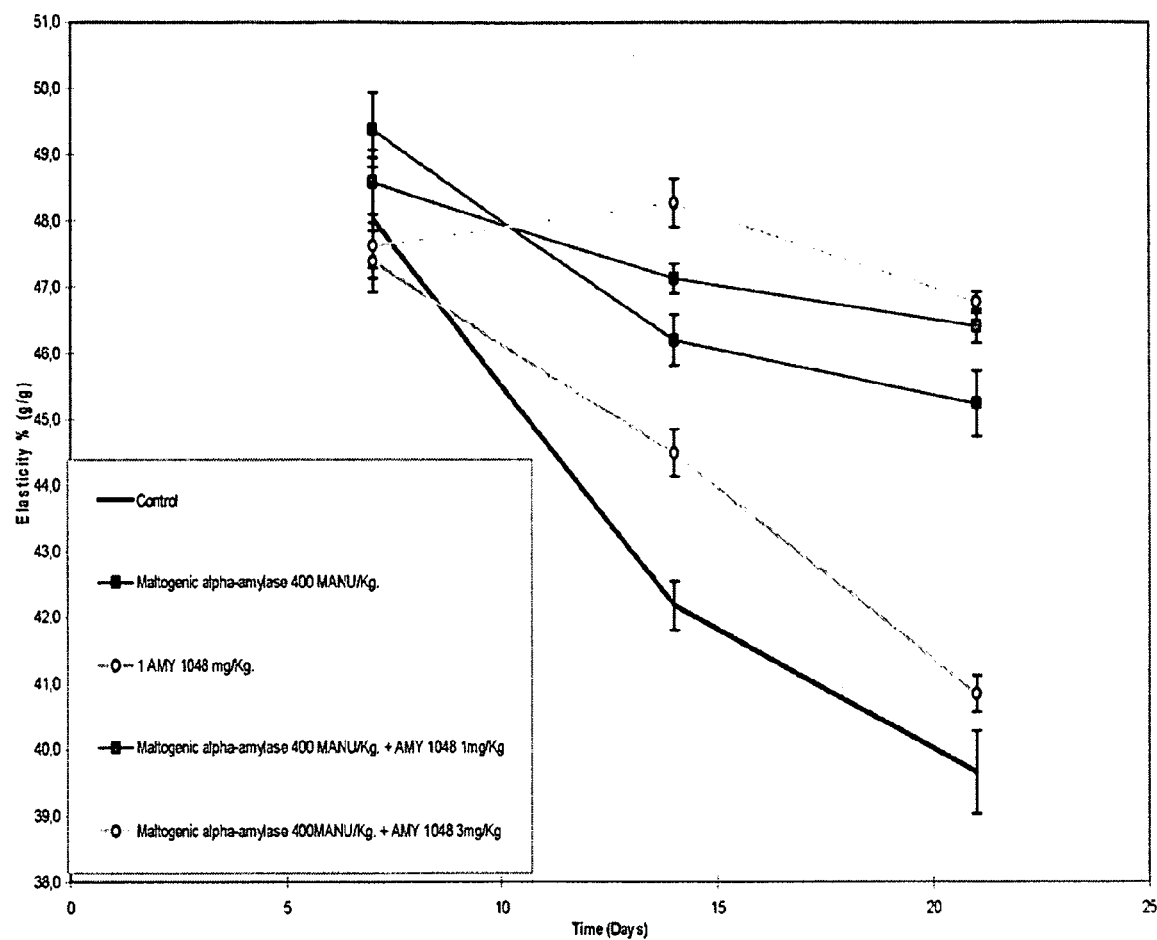
FIG. 2 shows the elasticity of bread crumb during 21 days of storage with and without AMY1048 of the invention and/or Maltogenic alpha-amylase.

Texture and water migration by NMR were measured on day 7, 14 and 21. A small sensory evaluation of softness and moistness was performed on day 21. The results of the tests are presented in FIG. 1 and FIG. 2.

The figures show that AMY1048 has a significant effect on firmness both alone and in combination with maltogenic alpha-amylase, furthermore the elasticity is at least comparable to or better than that of maltogenic alpha-amylase after 21 days of storage.

Figure 3:
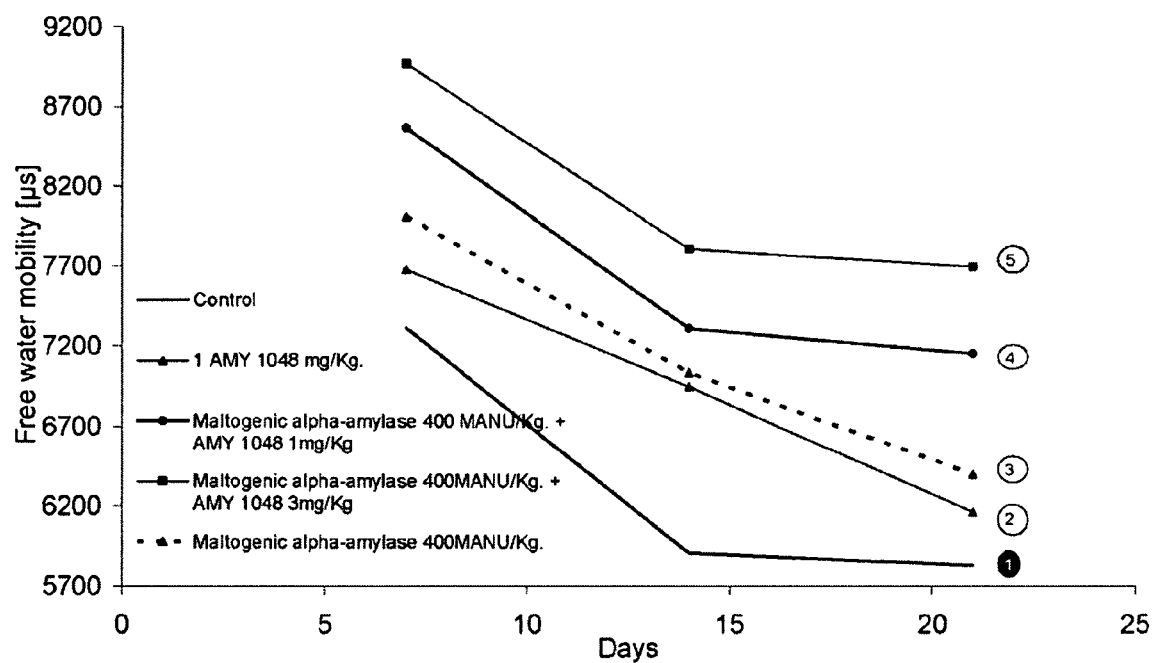
FIG. 3 shows the effect of the AMY1048 of the invention on the amount of free water with and without AMY1048 of the invention and/or Maltogenic alpha-amylase. The ranking from the small sensory is given in circles next to each curve. The highest ranking is given to the moistest bread.

FIG. 3 shows the effect of the enzymes on amount of free water. The ranking from the small sensory is given in circles next to each curve. The highest ranking is given to the moistest bread.

The NMR data on free water do correlate with the perceived moistness of bread crumb, which can be seen from the ranking of bread in Table 2 below and also shown in circles on the NMR graph.

TABLE 2

| Sensory ranking of moistness of bread crumb | |
|---|---|
| Bread No.: | Moistness |
| Control | 1 |
| AMY 1048 1 mg | 2 |
| Maltogenic alpha-amylase + AMY 1048 1 mg | 4 |
| Maltogenic alpha-amylase + AMY 1048 3 mg | 5 |
| Maltogenic alpha-amylase | 3 |

The data shows that the AMY1048 alpha-amylase improves softness and moistness of bread crumb alone and in combination with a maltogenic alpha-amylase.

Example 2

Conversion of granular wheat starch into glucose was performed using a glucoamylase (200 AGU/kg DS), an acid fungal amylase (50 AFAU/kg DS) and the alpha-amylase shown in SEQ ID NO:2 (100 KNU/kg DS). A slurry with 33% dry solids (DS) granular starch was prepared by adding 247.5 g of wheat starch under stirring to 502.5 ml of water. The pH was adjusted with HCl to 4.5. The granular starch slurry was distributed to 100 ml blue cap flasks with 75 g in each flask. The flasks were incubated with magnetic stirring in a 60° C. water bath. At zero hours the enzyme activities were dosed to the flasks. Samples were withdrawn after 24, 46, 70, and 90 hours.

Total dry solids starch was determined using the following method. The starch was completely hydrolyzed by adding an excess amount of alpha-amylase (300 KNU/Kg dry solids) and placing the sample in an oil bath at 95° C. for 45 minutes. Subsequently the samples were cooled to 60° C. and an excess amount of glucoamylase (600 AGU/kg DS) was added followed by incubation for 2 hours at 60° C.

Soluble dry solids in the starch hydrolysate were determined by refractive index measurement on samples after filtering through a 0.22 microM filter. The sugar profiles were determined by HPLC. The sugar composition of the starch hydrolysates was determined by HPLC and glucose yield was subsequently calculated as DX.

The results are shown in table 3 and 4.

TABLE 3

Soluble dry solids as percentage of total dry substance. Enzymes: glucoamylase, fungal acid amylase and the alpha-amylase (SEQ ID NO: 2).

|  | 24 hours | 46 hours | 70 hours | 90 hours |
|---|---|---|---|---|
| With CBD | 94.1 | 95.2 | 96.9 | 97.1 |

TABLE 4

The DX of the soluble hydrolysate: Enzymes: glucoamylase, fungal acid amylase and bacterial alpha-amylase with the alpha-amylase (SEQ ID NO: 2).

|  | 24 hours | 46 hours | 70 hours | 90 hours |
|---|---|---|---|---|
| With CBD | 89.9 | 93.3 | 93.0 | 93.2 |

Example 3

Desizing

Cotton woven fabric twill (270 g/m²) was obtained from Boras Inc, Sweden. The warp yarn of this fabric contained 8% starch and starch-based size (% dry weight/weight of fabric). Fabric was cut into about 65×25 cm×cm swatches. A 25 mM buffer pH7.0 was made from dissolving 20.7 gram NaHPO$_4$H$_2$O (Aldrich) in 6 liter de-ionized water and adjusting the pH with NaOH. About 1 mM CaCl$_2$ (Fisher) and 3 ml surfactant Kieralon Jet B (BASF) were added in the buffer solution.

The fabric swatch was immersed in the buffer solution (2 liters) for about 30 seconds at 40° C. and then impregnated through a padder to obtain a 100% vet pickup. The fabric swatch was then incubated in a temperature controlled chamber at 70° C. for hour. It was then washed at 90° C. through four washing boxes for total 16 minutes. The fabric swatch was then air dried.

To test starch residue on fabric, a swatch was cut and immersed in iodine solution for 60 seconds at room temperature, and it was rinsed in de-ionized water for about 10 seconds. After pressing out excess water from the fabric, the blue color formed on fabric swatch was compared to a standard photos ranged from 1 to 9, where 1 indicated heavy blue color and 9 indicated white color. The number (Tegewa) assigned to the treated swatch was 3. The Iodine solution was made by dissolving 10 g potassium iodine. KI, in 100 ml de-ionized water first, then adding 0.635 g iodine, J$_2$, and completely dissolving this under agitation, then diluting with de-ionized water to 800 ml and adding 200 ml ethanol, 96%, to improve wetting. The solution was stored in a brown glass bottle.

Example 4

Desizing with AMY1048

The same fabric was used as in Example 3. The buffer solution containing the CaCl, and surfactant was made the exactly the same as in Example 3. In addition, 4.8 mg/L AMY1048 amylase was added in the solution. The fabric was treated and assessed using the same procedure as in Example 3. The Tegewa number was 5, indicating a much more starch removal from the fabric treated in this example than in Example 3.

Example 5

Desizing with AMY1048

The same fabric was used as in Example 3. The buffer solution containing the CaCl$_2$ and surfactant was made the exactly the same as in Example 3. In addition, 12 mg/L Amyl 1048 amylase was added in the solution. The fabric was treated and assessed using the same procedure as in Example 3. The Tegewa number was 6.5, indicating a much more starch removal from the fabric treated in this example than in Example 4.

The invention claimed is:

1. An isolated polypeptide having alpha-amylase activity, which:
   (a) has at least 97% sequence identity with the sequence of amino acids 1 to 583 of SEQ ID NO: 6; or
   (b) is a fragment of the sequence of amino acids 1 to 583 of SEQ ID NO: 6 that has alpha-amylase activity.

2. The polypeptide of claim 1, which has at least 97% sequence identity with the sequence of amino acids 1 to 583 of SEQ ID NO: 6.

3. The polypeptide of claim 1, which has at least 98% sequence identity with the sequence of amino acids 1 to 583 of SEQ ID NO: 6.

4. The polypeptide of claim 1, which has at least 99% sequence identity with the sequence of amino acids 1 to 583 of SEQ ID NO: 6.

5. The polypeptide of claim 1, which is a fragment of the sequence of amino acids 1 to 583 of SEQ ID NO: 6 that has alpha-amylase activity.

6. The polypeptide of claim 1, which comprises the sequence of amino acids 1 to 583 of SEQ ID NO: 6.

7. The polypeptide of claim 1, which consists of the sequence of amino acids 1 to 583 of SEQ ID NO: 6.

8. A cleaning or detergent composition comprising a polypeptide of claim 1 and a surfactant.

9. An isolated polypeptide having carbohydrate-binding affinity, which comprises a carbohydrate binding domain which:
   (a) has at least 95% sequence identity with the sequence of amino acids 455 to 583 of SEQ ID NO: 6;
   (b) is a fragment of the sequence of amino acids 455 to 583 of SEQ ID NO: 6 that has carbohydrate binding activity.

10. The polypeptide of claim 9, wherein the carbohydrate-binding affinity is starch-binding affinity.

11. The polypeptide of claim 9, wherein the carbohydrate binding domain has at least 95% sequence identity with the sequence of amino acids 455 to 583 of SEQ ID NO: 6.

12. The polypeptide of claim 9, wherein the carbohydrate binding domain has at least 96% sequence identity with the sequence of amino acids 455 to 583 of SEQ ID NO: 6.

13. The polypeptide of claim 9, wherein the carbohydrate binding domain has at least 97% sequence identity with the sequence of amino acids 455 to 583 of SEQ ID NO: 6.

14. The polypeptide of claim 9, wherein the carbohydrate binding domain has at least 98% sequence identity with the sequence of amino acids 455 to 583 of SEQ ID NO: 6.

15. The polypeptide of claim 9, wherein the carbohydrate binding domain has at least 99% sequence identity with the sequence of amino acids 455 to 583 of SEQ ID NO: 6.

16. The polypeptide of claim 9, wherein the carbohydrate binding domain comprises the sequence of amino acids 455 to 583 of SEQ ID NO: 6.

17. The polypeptide of claim 9, wherein the carbohydrate binding domain consists of the sequence of amino acids 455 to 583 of SEQ ID NO: 6.

\* \* \* \* \*

SEQUENCE LISTING

```
<160> NUMBER OF SEQ ID NOS: 6

<210> SEQ ID NO 1
<211> LENGTH: 1860
<212> TYPE: DNA
<213> ORGANISM: Bacillus flavothermus
<220> FEATURE:
<221> NAME/KEY: CDS
<222> LOCATION: (1)..(1857)
<223> OTHER INFORMATION: AMY1048
<220> FEATURE:
<221> NAME/KEY: sig_peptide
<222> LOCATION: (1)..(99)
<220> FEATURE:
<221> NAME/KEY: mat_peptide
<222> LOCATION: (100)..(1857)
<220> FEATURE:
<221> NAME/KEY: misc_feature
<222> LOCATION: (100)..(1551)
<223> OTHER INFORMATION: Catalytic domain
<220> FEATURE:
<221> NAME/KEY: misc_feature
<222> LOCATION: (1552)..(1857)
<223> OTHER INFORMATION: Carbohydrate Binding Domain

<400> SEQUENCE: 1 atg tcc cta ttc aaa aaa agc ttt ccg tgg att tta tcc cta ctt ctt      48
Met Ser Leu Phe Lys Lys Ser Phe Pro Trp Ile Leu Ser Leu Leu Leu
             -30                 -25                 -20 ttg ttt tcg ttt att gct cct ttt tcc att caa aca gaa aaa gtc cga      96
Leu Phe Ser Phe Ile Ala Pro Phe Ser Ile Gln Thr Glu Lys Val Arg
         -15                 -10                  -5 gct gga agt gtg ccg gta aat ggc aca atg atg caa tat ttc gaa tgg     144
Ala Gly Ser Val Pro Val Asn Gly Thr Met Met Gln Tyr Phe Glu Trp
 -1   1               5                  10                  15 tac ctt cca gac gat gga aca cta tgg acg aaa gta gca aat aac gct     192
Tyr Leu Pro Asp Asp Gly Thr Leu Trp Thr Lys Val Ala Asn Asn Ala
                 20                  25                  30
```

-continued

| | | | | | | | | | | | | | | | | |
|---|---|---|---|---|---|---|---|---|---|---|---|---|---|---|---|---|
| caa | tct | tta | gcg | aat | ctt | ggc | att | act | gcc | ctt | tgg | ctt | ccc | cct | gcc | 240 |
| Gln | Ser | Leu | Ala | Asn | Leu | Gly | Ile | Thr | Ala | Leu | Trp | Leu | Pro | Pro | Ala | |
| | | 35 | | | | 40 | | | | | 45 | | | | | |
| tat | aaa | gga | aca | agc | agc | agt | gac | gtt | gga | tat | ggc | gtt | tat | gat | tta | 288 |
| Tyr | Lys | Gly | Thr | Ser | Ser | Ser | Asp | Val | Gly | Tyr | Gly | Val | Tyr | Asp | Leu | |
| | 50 | | | | | 55 | | | | | 60 | | | | | |
| tat | gac | ctt | gga | gag | ttt | aat | caa | aaa | gga | act | gtc | cga | aca | aaa | tac | 336 |
| Tyr | Asp | Leu | Gly | Glu | Phe | Asn | Gln | Lys | Gly | Thr | Val | Arg | Thr | Lys | Tyr | |
| 65 | | | | | 70 | | | | | 75 | | | | | | |
| ggg | aca | aaa | aca | caa | tat | atc | caa | gca | atc | caa | gcg | gcg | cat | aca | gca | 384 |
| Gly | Thr | Lys | Thr | Gln | Tyr | Ile | Gln | Ala | Ile | Gln | Ala | Ala | His | Thr | Ala | |
| 80 | | | | 85 | | | | | 90 | | | | | 95 | | |
| ggg | atg | caa | gta | tat | gca | gat | gtc | gtc | ttt | aac | cat | aaa | gcc | ggt | gca | 432 |
| Gly | Met | Gln | Val | Tyr | Ala | Asp | Val | Val | Phe | Asn | His | Lys | Ala | Gly | Ala | |
| | | | | 100 | | | | | 105 | | | | | 110 | | |
| gat | gga | aca | gaa | cta | gtc | gat | gca | gta | gaa | gta | aat | cct | tct | gac | cgc | 480 |
| Asp | Gly | Thr | Glu | Leu | Val | Asp | Ala | Val | Glu | Val | Asn | Pro | Ser | Asp | Arg | |
| | | | 115 | | | | | 120 | | | | | 125 | | | |
| aat | caa | gaa | ata | tca | gga | aca | tat | caa | atc | caa | gcg | tgg | aca | aaa | ttt | 528 |
| Asn | Gln | Glu | Ile | Ser | Gly | Thr | Tyr | Gln | Ile | Gln | Ala | Trp | Thr | Lys | Phe | |
| | | | 130 | | | | | 135 | | | | | 140 | | | |
| gat | ttt | cct | ggt | cgt | gga | aac | acc | tat | tct | agt | ttt | aaa | tgg | cgt | tgg | 576 |
| Asp | Phe | Pro | Gly | Arg | Gly | Asn | Thr | Tyr | Ser | Ser | Phe | Lys | Trp | Arg | Trp | |
| 145 | | | | | 150 | | | | | 155 | | | | | | |
| tat | cat | ttc | gat | gga | acg | gac | tgg | gat | gag | agt | aga | aaa | cta | aat | cgt | 624 |
| Tyr | His | Phe | Asp | Gly | Thr | Asp | Trp | Asp | Glu | Ser | Arg | Lys | Leu | Asn | Arg | |
| 160 | | | | | 165 | | | | | 170 | | | | | 175 | |
| att | tac | aag | ttc | cgc | ggc | acg | gga | aaa | gca | tgg | gat | tgg | gaa | gta | gat | 672 |
| Ile | Tyr | Lys | Phe | Arg | Gly | Thr | Gly | Lys | Ala | Trp | Asp | Trp | Glu | Val | Asp | |
| | | | | 180 | | | | | 185 | | | | | 190 | | |
| aca | gaa | aac | ggg | aat | tat | gac | tat | ctc | atg | tat | gca | gat | tta | gat | atg | 720 |
| Thr | Glu | Asn | Gly | Asn | Tyr | Asp | Tyr | Leu | Met | Tyr | Ala | Asp | Leu | Asp | Met | |
| | | | 195 | | | | | 200 | | | | | 205 | | | |
| gat | cat | cca | gag | gtt | gta | tcc | gaa | cta | aaa | aat | tgg | gga | aag | tgg | tat | 768 |
| Asp | His | Pro | Glu | Val | Val | Ser | Glu | Leu | Lys | Asn | Trp | Gly | Lys | Trp | Tyr | |
| | | | 210 | | | | | 215 | | | | | 220 | | | |
| gta | acc | aca | acc | aat | atc | gac | gga | ttc | cgt | ctg | gat | gca | gtg | aag | cat | 816 |
| Val | Thr | Thr | Thr | Asn | Ile | Asp | Gly | Phe | Arg | Leu | Asp | Ala | Val | Lys | His | |
| | | 225 | | | | | 230 | | | | | 235 | | | | |
| att | aaa | tat | agc | ttt | ttc | ccg | gac | tgg | cta | tcg | tac | gta | cga | acc | caa | 864 |
| Ile | Lys | Tyr | Ser | Phe | Phe | Pro | Asp | Trp | Leu | Ser | Tyr | Val | Arg | Thr | Gln | |
| 240 | | | | | 245 | | | | | 250 | | | | | 255 | |
| aca | caa | aag | cct | ctt | ttt | gcc | gtt | ggg | gaa | ttt | tgg | agc | tat | gac | att | 912 |
| Thr | Gln | Lys | Pro | Leu | Phe | Ala | Val | Gly | Glu | Phe | Trp | Ser | Tyr | Asp | Ile | |
| | | | | 260 | | | | | 265 | | | | | 270 | | |
| agc | aag | ttg | cac | aac | tat | att | aca | aag | acg | aac | ggc | tct | atg | tcc | cta | 960 |
| Ser | Lys | Leu | His | Asn | Tyr | Ile | Thr | Lys | Thr | Asn | Gly | Ser | Met | Ser | Leu | |
| | | | 275 | | | | | 280 | | | | | 285 | | | |
| ttc | gat | gcc | ccg | ctg | cat | aac | aat | ttt | tat | ata | gca | tcg | aaa | tca | ggc | 1008 |
| Phe | Asp | Ala | Pro | Leu | His | Asn | Asn | Phe | Tyr | Ile | Ala | Ser | Lys | Ser | Gly | |
| | | | 290 | | | | | 295 | | | | | 300 | | | |
| ggt | tat | ttt | gat | atg | cgc | aca | tta | ctc | aac | aac | aca | ttg | atg | aaa | gat | 1056 |
| Gly | Tyr | Phe | Asp | Met | Arg | Thr | Leu | Leu | Asn | Asn | Thr | Leu | Met | Lys | Asp | |
| | | 305 | | | | | 310 | | | | | 315 | | | | |
| cag | cct | aca | tta | gca | gtc | aca | tta | gtg | gat | aat | cac | gat | act | gag | cca | 1104 |
| Gln | Pro | Thr | Leu | Ala | Val | Thr | Leu | Val | Asp | Asn | His | Asp | Thr | Glu | Pro | |
| 320 | | | | 325 | | | | | 330 | | | | | 335 | | |
| ggg | caa | tct | ctg | cag | tca | tgg | gtc | gag | cca | tgg | ttt | aaa | ccg | tta | gct | 1152 |
| Gly | Gln | Ser | Leu | Gln | Ser | Trp | Val | Glu | Pro | Trp | Phe | Lys | Pro | Leu | Ala | |

-continued

```
                      340                 345                 350
tac gca ttt atc ttg acc cgc caa gaa ggt tat cct tgc gtc ttt tat    1200
Tyr Ala Phe Ile Leu Thr Arg Gln Glu Gly Tyr Pro Cys Val Phe Tyr
            355                 360                 365 gga gat tac tat ggt att cca aaa tac aac att cct gcg ctg aaa agc    1248
Gly Asp Tyr Tyr Gly Ile Pro Lys Tyr Asn Ile Pro Ala Leu Lys Ser
        370                 375                 380 aaa ctt gat ccg ctg tta att gcc aga aga gat tat gcc tat gga aca    1296
Lys Leu Asp Pro Leu Leu Ile Ala Arg Arg Asp Tyr Ala Tyr Gly Thr
385                 390                 395 cag cac gac tat att gac agt gcg gat att atc ggt tgg acg cgg gaa    1344
Gln His Asp Tyr Ile Asp Ser Ala Asp Ile Ile Gly Trp Thr Arg Glu
400                 405                 410                 415 gga gtg gct gaa aaa gca aat tca gga ctg gct gca ctc att acc gac    1392
Gly Val Ala Glu Lys Ala Asn Ser Gly Leu Ala Ala Leu Ile Thr Asp
            420                 425                 430 ggg cct ggc gga agc aaa tgg atg tat gtt gga aaa caa cac gct ggc    1440
Gly Pro Gly Gly Ser Lys Trp Met Tyr Val Gly Lys Gln His Ala Gly
        435                 440                 445 aaa acg ttt tat gat tta acc ggc aat cga agt gat aca gtg aca atc    1488
Lys Thr Phe Tyr Asp Leu Thr Gly Asn Arg Ser Asp Thr Val Thr Ile
450                 455                 460 aat gct gat gga tgg gga gaa ttt aaa gtc aat gga ggg tct gta tcc    1536
Asn Ala Asp Gly Trp Gly Glu Phe Lys Val Asn Gly Gly Ser Val Ser
465                 470                 475 ata tgg gtt cca aaa ata tca acc act tcc caa ata aca ttt act gta    1584
Ile Trp Val Pro Lys Ile Ser Thr Thr Ser Gln Ile Thr Phe Thr Val
480                 485                 490                 495 aat aac gcc aca acc gtt tgg gga caa aat gta tac gtt gtc ggg aat    1632
Asn Asn Ala Thr Thr Val Trp Gly Gln Asn Val Tyr Val Val Gly Asn
            500                 505                 510 att tcg cag ctg ggg aac tgg gat cca gtc cac gca gtt caa atg acg    1680
Ile Ser Gln Leu Gly Asn Trp Asp Pro Val His Ala Val Gln Met Thr
        515                 520                 525 ccg tct tct tat cca aca tgg act gta aca atc cct ctt ctt caa ggg    1728
Pro Ser Ser Tyr Pro Thr Trp Thr Val Thr Ile Pro Leu Leu Gln Gly
530                 535                 540 caa aac ata caa ttt aaa ttt atc aaa aaa gat tca gct gga aat gtc    1776
Gln Asn Ile Gln Phe Lys Phe Ile Lys Lys Asp Ser Ala Gly Asn Val
545                 550                 555 att tgg gaa gat ata tcg aat cga aca tac acc gtc cca act gct gca    1824
Ile Trp Glu Asp Ile Ser Asn Arg Thr Tyr Thr Val Pro Thr Ala Ala
560                 565                 570                 575 tcc gga gca tat aca gcc agc tgg aac gtg ccc tag                    1860
Ser Gly Ala Tyr Thr Ala Ser Trp Asn Val Pro
            580                 585

<210> SEQ ID NO 2
<211> LENGTH: 619
<212> TYPE: PRT
<213> ORGANISM: Bacillus flavothermus

<400> SEQUENCE: 2

Met Ser Leu Phe Lys Lys Ser Phe Pro Trp Ile Leu Ser Leu Leu Leu
                -30                 -25                 -20

Leu Phe Ser Phe Ile Ala Pro Phe Ser Ile Gln Thr Glu Lys Val Arg
            -15                 -10                 -5

Ala Gly Ser Val Pro Val Asn Gly Thr Met Met Gln Tyr Phe Glu Trp
-1   1               5                  10                  15
```

-continued

```
Tyr Leu Pro Asp Asp Gly Thr Leu Trp Thr Lys Val Ala Asn Asn Ala
             20                  25                  30

Gln Ser Leu Ala Asn Leu Gly Ile Thr Ala Leu Trp Leu Pro Pro Ala
         35                  40                  45

Tyr Lys Gly Thr Ser Ser Asp Val Gly Tyr Gly Val Tyr Asp Leu
             50                  55                  60

Tyr Asp Leu Gly Glu Phe Asn Gln Lys Gly Thr Val Arg Thr Lys Tyr
 65                  70                  75

Gly Thr Lys Thr Gln Tyr Ile Gln Ala Ile Gln Ala His Thr Ala
 80                  85                  90                  95

Gly Met Gln Val Tyr Ala Asp Val Val Phe Asn His Lys Ala Gly Ala
                100                 105                 110

Asp Gly Thr Glu Leu Val Asp Ala Val Glu Val Asn Pro Ser Asp Arg
            115                 120                 125

Asn Gln Glu Ile Ser Gly Thr Tyr Gln Ile Gln Ala Trp Thr Lys Phe
        130                 135                 140

Asp Phe Pro Gly Arg Gly Asn Thr Tyr Ser Ser Phe Lys Trp Arg Trp
    145                 150                 155

Tyr His Phe Asp Gly Thr Asp Trp Asp Glu Ser Arg Lys Leu Asn Arg
160                 165                 170                 175

Ile Tyr Lys Phe Arg Gly Thr Gly Lys Ala Trp Asp Trp Glu Val Asp
                180                 185                 190

Thr Glu Asn Gly Asn Tyr Asp Tyr Leu Met Tyr Ala Asp Leu Asp Met
            195                 200                 205

Asp His Pro Glu Val Val Ser Glu Leu Lys Asn Trp Gly Lys Trp Tyr
        210                 215                 220

Val Thr Thr Thr Asn Ile Asp Gly Phe Arg Leu Asp Ala Val Lys His
    225                 230                 235

Ile Lys Tyr Ser Phe Phe Pro Asp Trp Leu Ser Tyr Val Arg Thr Gln
240                 245                 250                 255

Thr Gln Lys Pro Leu Phe Ala Val Gly Glu Phe Trp Ser Tyr Asp Ile
                260                 265                 270

Ser Lys Leu His Asn Tyr Ile Thr Lys Thr Asn Gly Ser Met Ser Leu
            275                 280                 285

Phe Asp Ala Pro Leu His Asn Asn Phe Tyr Ile Ala Ser Lys Ser Gly
        290                 295                 300

Gly Tyr Phe Asp Met Arg Thr Leu Leu Asn Asn Thr Leu Met Lys Asp
    305                 310                 315

Gln Pro Thr Leu Ala Val Thr Leu Val Asp Asn His Asp Thr Glu Pro
320                 325                 330                 335

Gly Gln Ser Leu Gln Ser Trp Val Glu Pro Trp Phe Lys Pro Leu Ala
                340                 345                 350

Tyr Ala Phe Ile Leu Thr Arg Gln Glu Gly Tyr Pro Cys Val Phe Tyr
            355                 360                 365

Gly Asp Tyr Tyr Gly Ile Pro Lys Tyr Asn Ile Pro Ala Leu Lys Ser
        370                 375                 380

Lys Leu Asp Pro Leu Leu Ile Ala Arg Arg Asp Tyr Ala Tyr Gly Thr
    385                 390                 395

Gln His Asp Tyr Ile Asp Ser Ala Asp Ile Ile Gly Trp Thr Arg Glu
400                 405                 410                 415

Gly Val Ala Glu Lys Ala Asn Ser Gly Leu Ala Ala Leu Ile Thr Asp
                420                 425                 430

Gly Pro Gly Gly Ser Lys Trp Met Tyr Val Gly Lys Gln His Ala Gly
```

-continued

```
                435                 440                 445
Lys Thr Phe Tyr Asp Leu Thr Gly Asn Arg Ser Asp Thr Val Thr Ile
            450                 455                 460

Asn Ala Asp Gly Trp Gly Glu Phe Lys Val Asn Gly Gly Ser Val Ser
465                 470                 475

Ile Trp Val Pro Lys Ile Ser Thr Ser Gln Ile Thr Phe Thr Val
480                 485                 490                 495

Asn Asn Ala Thr Thr Val Trp Gly Gln Asn Val Tyr Val Val Gly Asn
                500                 505                 510

Ile Ser Gln Leu Gly Asn Trp Asp Pro Val His Ala Val Gln Met Thr
            515                 520                 525

Pro Ser Ser Tyr Pro Thr Trp Thr Val Thr Ile Pro Leu Leu Gln Gly
            530                 535                 540

Gln Asn Ile Gln Phe Lys Phe Ile Lys Lys Asp Ser Ala Gly Asn Val
            545                 550                 555

Ile Trp Glu Asp Ile Ser Asn Arg Thr Tyr Thr Val Pro Thr Ala Ala
560                 565                 570                 575

Ser Gly Ala Tyr Thr Ala Ser Trp Asn Val Pro
                580                 585
```

<210> SEQ ID NO 3
<211> LENGTH: 1728
<212> TYPE: DNA
<213> ORGANISM: Bacillus sp.
<220> FEATURE:
<221> NAME/KEY: CDS
<222> LOCATION: (1)..(1725)
<223> OTHER INFORMATION: AMY1039
<220> FEATURE:
<221> NAME/KEY: sig_peptide
<222> LOCATION: (1)..(99)
<220> FEATURE:
<221> NAME/KEY: mat_peptide
<222> LOCATION: (100)..(1725)
<220> FEATURE:
<221> NAME/KEY: misc_feature
<222> LOCATION: (100)..(1551)
<223> OTHER INFORMATION: Catalytic domain
<220> FEATURE:
<221> NAME/KEY: misc_feature
<222> LOCATION: (1552)..(1725)
<223> OTHER INFORMATION: Binding Domain

<400> SEQUENCE: 3

```
atg tcc cta ttc aaa aaa atc ttt ccg tgg att tta tcc cta ctt ctt      48
Met Ser Leu Phe Lys Lys Ile Phe Pro Trp Ile Leu Ser Leu Leu Leu
        -30                 -25                 -20 ttg ttt ttg ttt att gct cct ttt tcc att caa aca gaa aaa gtc cga      96
Leu Phe Leu Phe Ile Ala Pro Phe Ser Ile Gln Thr Glu Lys Val Arg
    -15                 -10                 -5 gct gga agt gtg ccg gta aat ggc aca atg atg caa tat ttc gaa tgg     144
Ala Gly Ser Val Pro Val Asn Gly Thr Met Met Gln Tyr Phe Glu Trp
 -1  1               5                  10                  15 tac ctt cca gac gat gga aca cta tgg acg aaa gta gca aat aac gcc     192
Tyr Leu Pro Asp Asp Gly Thr Leu Trp Thr Lys Val Ala Asn Asn Ala
                20                  25                  30 caa tct tta gcg aat ctc ggc att act gcc ctt tgg ctt ccc cct gcc     240
Gln Ser Leu Ala Asn Leu Gly Ile Thr Ala Leu Trp Leu Pro Pro Ala
            35                  40                  45 tat aaa gga aca agc agc agt gac gtt gga tat ggg gtt tat gat tta     288
Tyr Lys Gly Thr Ser Ser Ser Asp Val Gly Tyr Gly Val Tyr Asp Leu
        50                  55                  60
```

```
tat gac ctt gga gag ttt aat caa aaa gga act gtc cga aca aaa tac      336
Tyr Asp Leu Gly Glu Phe Asn Gln Lys Gly Thr Val Arg Thr Lys Tyr
     65                  70                  75 ggg aca aaa aca caa tat atc caa gca atc caa gcg gcg cat aca gca      384
Gly Thr Lys Thr Gln Tyr Ile Gln Ala Ile Gln Ala Ala His Thr Ala
 80                  85                  90                  95 ggg atg caa gta tat gca gat gtc gtc ttt aac cat aaa gcc ggt gca      432
Gly Met Gln Val Tyr Ala Asp Val Val Phe Asn His Lys Ala Gly Ala
                    100                 105                 110 gat gga aca gaa cta gtc gat gca gta gaa gta aat cct tct gac cgc      480
Asp Gly Thr Glu Leu Val Asp Ala Val Glu Val Asn Pro Ser Asp Arg
                115                 120                 125 aat caa gaa ata tca gga aca tat caa atc caa gcg tgg aca aaa ttt      528
Asn Gln Glu Ile Ser Gly Thr Tyr Gln Ile Gln Ala Trp Thr Lys Phe
            130                 135                 140 gat ttt cct ggt cgt gga aac acc tat tct agt ttt aaa tgg cgt tgg      576
Asp Phe Pro Gly Arg Gly Asn Thr Tyr Ser Ser Phe Lys Trp Arg Trp
145                 150                 155 tat cat ttc gat gga acg gac tgg gat gag agt aga aaa cta aat cgt      624
Tyr His Phe Asp Gly Thr Asp Trp Asp Glu Ser Arg Lys Leu Asn Arg
160                 165                 170                 175 att tac aag ttc cgc ggc acg gga aaa gca tgg gat tgg gaa gta gat      672
Ile Tyr Lys Phe Arg Gly Thr Gly Lys Ala Trp Asp Trp Glu Val Asp
                    180                 185                 190 aca gaa aac ggg aat tat gac tat ctc atg tat gca gat tta gat atg      720
Thr Glu Asn Gly Asn Tyr Asp Tyr Leu Met Tyr Ala Asp Leu Asp Met
                195                 200                 205 gat cat cca gag gtt gta tcc gaa cta aaa aat tgg gga aag tgg tat      768
Asp His Pro Glu Val Val Ser Glu Leu Lys Asn Trp Gly Lys Trp Tyr
            210                 215                 220 gta acc aca acc aat atc gac gga ttc cgt ctg gat gca gtg aag cat      816
Val Thr Thr Thr Asn Ile Asp Gly Phe Arg Leu Asp Ala Val Lys His
225                 230                 235 att aaa tat agc ttt ttc ccg gac tgg cta tcg tac gta cga acc caa      864
Ile Lys Tyr Ser Phe Phe Pro Asp Trp Leu Ser Tyr Val Arg Thr Gln
240                 245                 250                 255 aca caa aag cct ctt ttt gcc gtt ggg gaa ttt tgg agc tat gac att      912
Thr Gln Lys Pro Leu Phe Ala Val Gly Glu Phe Trp Ser Tyr Asp Ile
                    260                 265                 270 agc aag ctg cac aac tat att aca aag acg aac ggc tct atg tcc cta      960
Ser Lys Leu His Asn Tyr Ile Thr Lys Thr Asn Gly Ser Met Ser Leu
                275                 280                 285 ttc gat gcc ccg ctg cat aac aat ttt tat ata gca tcg aaa tca ggc     1008
Phe Asp Ala Pro Leu His Asn Asn Phe Tyr Ile Ala Ser Lys Ser Gly
            290                 295                 300 ggt tat ttt gat atg cgc aca tta ctc aac aac aca ttg atg aaa gat     1056
Gly Tyr Phe Asp Met Arg Thr Leu Leu Asn Asn Thr Leu Met Lys Asp
305                 310                 315 cag cct aca tta gca gtc aca tta gtg gat aat cac gat act gag cca     1104
Gln Pro Thr Leu Ala Val Thr Leu Val Asp Asn His Asp Thr Glu Pro
320                 325                 330                 335 ggg caa tct ttg cag tca tgg gtc gag cca tgg ttt aaa ccg tta gct     1152
Gly Gln Ser Leu Gln Ser Trp Val Glu Pro Trp Phe Lys Pro Leu Ala
                    340                 345                 350 tac gca ttt atc ttg acc cgc caa gaa ggt tat cct tgt gtc ttt tat     1200
Tyr Ala Phe Ile Leu Thr Arg Gln Glu Gly Tyr Pro Cys Val Phe Tyr
                355                 360                 365 gga gat tac tat ggt att cca aaa tac aac att cct gcg ctg aaa agc     1248
Gly Asp Tyr Tyr Gly Ile Pro Lys Tyr Asn Ile Pro Ala Leu Lys Ser
            370                 375                 380
```

```
aaa ctt gat ccg ctg tta att gcc aga aga gat tat gcc tat gga aca      1296
Lys Leu Asp Pro Leu Leu Ile Ala Arg Arg Asp Tyr Ala Tyr Gly Thr
        385                 390                 395 cag cac gac tat att gac agt gcg gat att atc ggt tgg acg cgg gaa      1344
Gln His Asp Tyr Ile Asp Ser Ala Asp Ile Ile Gly Trp Thr Arg Glu
400                 405                 410                 415 gga gtg gct gaa aaa gca aat tca gga ctg gct gca ctc att acc gac      1392
Gly Val Ala Glu Lys Ala Asn Ser Gly Leu Ala Ala Leu Ile Thr Asp
                420                 425                 430 ggg cct ggc gga agc aaa tgg atg tat gtt gga aaa caa cac gct ggc      1440
Gly Pro Gly Gly Ser Lys Trp Met Tyr Val Gly Lys Gln His Ala Gly
            435                 440                 445 aaa acg ttt tat gat tta acc ggc aat cga agt gat aca gtg aca atc      1488
Lys Thr Phe Tyr Asp Leu Thr Gly Asn Arg Ser Asp Thr Val Thr Ile
        450                 455                 460 aat gct gat gga tgg gga gaa ttt aaa gtc aat gga ggg tct gta tcc      1536
Asn Ala Asp Gly Trp Gly Glu Phe Lys Val Asn Gly Gly Ser Val Ser
465                 470                 475 ata tgg gtt cca aaa aca tca acc act tcc caa ata aca ttt act gta      1584
Ile Trp Val Pro Lys Thr Ser Thr Thr Ser Gln Ile Thr Phe Thr Val
480                 485                 490                 495 aat aat gcc aca acc gtt tgg gga caa aat gta tac gtt gtc ggg aat      1632
Asn Asn Ala Thr Thr Val Trp Gly Gln Asn Val Tyr Val Val Gly Asn
                500                 505                 510 att tcg cag ctg ggg aac tgg gat cca gtc aac gca gtt caa atg acg      1680
Ile Ser Gln Leu Gly Asn Trp Asp Pro Val Asn Ala Val Gln Met Thr
            515                 520                 525 ccg tct tct tat cca aca tgg gta gtg aca gtc cct ctt cca cag taa      1728
Pro Ser Ser Tyr Pro Thr Trp Val Val Thr Val Pro Leu Pro Gln
        530                 535                 540

<210> SEQ ID NO 4
<211> LENGTH: 575
<212> TYPE: PRT
<213> ORGANISM: Bacillus sp.

<400> SEQUENCE: 4

Met Ser Leu Phe Lys Lys Ile Phe Pro Trp Ile Leu Ser Leu Leu
            -30                 -25                 -20

Leu Phe Leu Phe Ile Ala Pro Phe Ser Ile Gln Thr Glu Lys Val Arg
        -15                 -10                  -5

Ala Gly Ser Val Pro Val Asn Gly Thr Met Met Gln Tyr Phe Glu Trp
-1   1               5                  10                  15

Tyr Leu Pro Asp Asp Gly Thr Leu Trp Thr Lys Val Ala Asn Asn Ala
                20                  25                  30

Gln Ser Leu Ala Asn Leu Gly Ile Thr Ala Leu Trp Leu Pro Pro Ala
            35                  40                  45

Tyr Lys Gly Thr Ser Ser Ser Asp Val Gly Tyr Gly Val Tyr Asp Leu
        50                  55                  60

Tyr Asp Leu Gly Glu Phe Asn Gln Lys Gly Thr Val Arg Thr Lys Tyr
65                  70                  75

Gly Thr Lys Thr Gln Tyr Ile Gln Ala Ile Gln Ala Ala His Thr Ala
80                  85                  90                  95

Gly Met Gln Val Tyr Ala Asp Val Val Phe Asn His Lys Ala Gly Ala
                100                 105                 110

Asp Gly Thr Glu Leu Val Asp Ala Val Glu Val Asn Pro Ser Asp Arg
            115                 120                 125
```

```
Asn Gln Glu Ile Ser Gly Thr Tyr Gln Ile Gln Ala Trp Thr Lys Phe
            130                 135                 140

Asp Phe Pro Gly Arg Gly Asn Thr Tyr Ser Ser Phe Lys Trp Arg Trp
        145                 150                 155

Tyr His Phe Asp Gly Thr Asp Trp Asp Glu Ser Arg Lys Leu Asn Arg
160                 165                 170                 175

Ile Tyr Lys Phe Arg Gly Thr Gly Lys Ala Trp Asp Trp Glu Val Asp
                180                 185                 190

Thr Glu Asn Gly Asn Tyr Asp Tyr Leu Met Tyr Ala Asp Leu Asp Met
                195                 200                 205

Asp His Pro Glu Val Val Ser Glu Leu Lys Asn Trp Gly Lys Trp Tyr
            210                 215                 220

Val Thr Thr Thr Asn Ile Asp Gly Phe Arg Leu Asp Ala Val Lys His
    225                 230                 235

Ile Lys Tyr Ser Phe Phe Pro Asp Trp Leu Ser Tyr Val Arg Thr Gln
240                 245                 250                 255

Thr Gln Lys Pro Leu Phe Ala Val Gly Glu Phe Trp Ser Tyr Asp Ile
                260                 265                 270

Ser Lys Leu His Asn Tyr Ile Thr Lys Thr Asn Gly Ser Met Ser Leu
                275                 280                 285

Phe Asp Ala Pro Leu His Asn Asn Phe Tyr Ile Ala Ser Lys Ser Gly
            290                 295                 300

Gly Tyr Phe Asp Met Arg Thr Leu Leu Asn Asn Thr Leu Met Lys Asp
    305                 310                 315

Gln Pro Thr Leu Ala Val Thr Leu Val Asp Asn His Asp Thr Glu Pro
320                 325                 330                 335

Gly Gln Ser Leu Gln Ser Trp Val Glu Pro Trp Phe Lys Pro Leu Ala
                340                 345                 350

Tyr Ala Phe Ile Leu Thr Arg Gln Glu Gly Tyr Pro Cys Val Phe Tyr
                355                 360                 365

Gly Asp Tyr Tyr Gly Ile Pro Lys Tyr Asn Ile Pro Ala Leu Lys Ser
            370                 375                 380

Lys Leu Asp Pro Leu Leu Ile Ala Arg Arg Asp Tyr Ala Tyr Gly Thr
    385                 390                 395

Gln His Asp Tyr Ile Asp Ser Ala Asp Ile Ile Gly Trp Thr Arg Glu
400                 405                 410                 415

Gly Val Ala Glu Lys Ala Asn Ser Gly Leu Ala Ala Leu Ile Thr Asp
                420                 425                 430

Gly Pro Gly Gly Ser Lys Trp Met Tyr Val Gly Lys Gln His Ala Gly
            435                 440                 445

Lys Thr Phe Tyr Asp Leu Thr Gly Asn Arg Ser Asp Thr Val Thr Ile
    450                 455                 460

Asn Ala Asp Gly Trp Gly Glu Phe Lys Val Asn Gly Gly Ser Val Ser
465                 470                 475

Ile Trp Val Pro Lys Thr Ser Thr Ser Gln Ile Thr Phe Thr Val
480                 485                 490                 495

Asn Asn Ala Thr Thr Val Trp Gly Gln Asn Val Tyr Val Val Gly Asn
                500                 505                 510

Ile Ser Gln Leu Gly Asn Trp Asp Pro Val Asn Ala Val Gln Met Thr
            515                 520                 525

Pro Ser Ser Tyr Pro Thr Trp Val Val Thr Val Pro Leu Pro Gln
    530                 535                 540
```

-continued

```
<210> SEQ ID NO 5
<211> LENGTH: 1842
<212> TYPE: DNA
<213> ORGANISM: Bacillus sp.
<220> FEATURE:
<221> NAME/KEY: CDS
<222> LOCATION: (1)..(1839)
<223> OTHER INFORMATION: AMY1079
<220> FEATURE:
<221> NAME/KEY: sig_peptide
<222> LOCATION: (1)..(90)
<220> FEATURE:
<221> NAME/KEY: mat_peptide
<222> LOCATION: (91)..(1839)
<220> FEATURE:
<221> NAME/KEY: misc_feature
<222> LOCATION: (91)..(1452)
<223> OTHER INFORMATION: Catalytic domain
<220> FEATURE:
<221> NAME/KEY: misc_feature
<222> LOCATION: (1453)..(1839)
<223> OTHER INFORMATION: binding domain

<400> SEQUENCE: 5
```

| | | | | | | | | | | | | | | | | |
|---|---|---|---|---|---|---|---|---|---|---|---|---|---|---|---|---|
| atg | agt | tat | ttg | aaa | aaa | gtg | tgg | ttg | tat | tac | acc | atc | atc | gct | acc | 48 |
| Met | Ser | Tyr | Leu | Lys | Lys | Val | Trp | Leu | Tyr | Tyr | Thr | Ile | Ile | Ala | Thr | |
| -30 | | | | -25 | | | | | -20 | | | | | -15 | | |
| tta | atc | att | tcc | ttt | ttc | aca | ccc | ttc | tca | act | gca | caa | gcg | aac | acc | 96 |
| Leu | Ile | Ile | Ser | Phe | Phe | Thr | Pro | Phe | Ser | Thr | Ala | Gln | Ala | Asn | Thr | |
| | | | -10 | | | | | -5 | | | | | -1 | 1 | | |
| gca | cca | gtc | aac | gga | acg | atg | atg | caa | tat | ttc | gaa | tgg | gat | tta | ccg | 144 |
| Ala | Pro | Val | Asn | Gly | Thr | Met | Met | Gln | Tyr | Phe | Glu | Trp | Asp | Leu | Pro | |
| | | 5 | | | | | 10 | | | | | 15 | | | | |
| aat | gat | ggc | aca | ctt | tgg | acg | aaa | gta | aaa | aac | gaa | gca | agc | agt | ctt | 192 |
| Asn | Asp | Gly | Thr | Leu | Trp | Thr | Lys | Val | Lys | Asn | Glu | Ala | Ser | Ser | Leu | |
| | 20 | | | | | 25 | | | | | 30 | | | | | |
| tct | gct | tta | ggt | att | act | gcc | tta | tgg | ttg | cca | cct | gca | tac | aaa | gga | 240 |
| Ser | Ala | Leu | Gly | Ile | Thr | Ala | Leu | Trp | Leu | Pro | Pro | Ala | Tyr | Lys | Gly | |
| 35 | | | | | 40 | | | | | 45 | | | | | 50 | |
| aca | agc | caa | gcg | gat | gtc | ggg | tat | ggc | gtg | tac | gat | ttg | tat | gac | cta | 288 |
| Thr | Ser | Gln | Ala | Asp | Val | Gly | Tyr | Gly | Val | Tyr | Asp | Leu | Tyr | Asp | Leu | |
| | | | | 55 | | | | | 60 | | | | | 65 | | |
| ggg | gaa | ttt | aat | caa | aaa | ggg | acg | att | cga | acg | aaa | tac | gga | aca | aaa | 336 |
| Gly | Glu | Phe | Asn | Gln | Lys | Gly | Thr | Ile | Arg | Thr | Lys | Tyr | Gly | Thr | Lys | |
| | | | 70 | | | | | 75 | | | | | 80 | | | |
| acg | caa | tat | tta | caa | gct | att | cag | gcg | gca | aaa | agc | gct | ggt | atg | caa | 384 |
| Thr | Gln | Tyr | Leu | Gln | Ala | Ile | Gln | Ala | Ala | Lys | Ser | Ala | Gly | Met | Gln | |
| | | | | 85 | | | | | 90 | | | | | 95 | | |
| gta | tat | gcc | gat | gtc | gta | ttt | aac | cat | aag | gca | ggg | gcg | gat | agt | aca | 432 |
| Val | Tyr | Ala | Asp | Val | Val | Phe | Asn | His | Lys | Ala | Gly | Ala | Asp | Ser | Thr | |
| | 100 | | | | | 105 | | | | | 110 | | | | | |
| gaa | tgg | gtt | gac | gca | gtc | gaa | gtg | aat | cct | tct | aac | cga | aat | caa | gaa | 480 |
| Glu | Trp | Val | Asp | Ala | Val | Glu | Val | Asn | Pro | Ser | Asn | Arg | Asn | Gln | Glu | |
| 115 | | | | | 120 | | | | | 125 | | | | | 130 | |
| aca | tct | ggc | aca | tat | caa | att | caa | gca | tgg | acc | aaa | ttt | gac | ttc | cct | 528 |
| Thr | Ser | Gly | Thr | Tyr | Gln | Ile | Gln | Ala | Trp | Thr | Lys | Phe | Asp | Phe | Pro | |
| | | | | 135 | | | | | 140 | | | | | 145 | | |
| ggt | cgc | gga | aac | aca | tac | tca | agc | ttc | aaa | tgg | cgc | tgg | tat | cat | ttt | 576 |
| Gly | Arg | Gly | Asn | Thr | Tyr | Ser | Ser | Phe | Lys | Trp | Arg | Trp | Tyr | His | Phe | |
| | | | 150 | | | | | 155 | | | | | 160 | | | |
| gac | ggt | acg | gat | tgg | gat | gaa | agc | cga | aaa | cta | aat | cgc | att | tac | aaa | 624 |
| Asp | Gly | Thr | Asp | Trp | Asp | Glu | Ser | Arg | Lys | Leu | Asn | Arg | Ile | Tyr | Lys | |
| | | | | 165 | | | | | 170 | | | | | 175 | | |
| ttt | cgt | ggc | aca | gga | aaa | gca | tgg | gat | tgg | gag | gta | gac | aca | gag | aac | 672 |
| Phe | Arg | Gly | Thr | Gly | Lys | Ala | Trp | Asp | Trp | Glu | Val | Asp | Thr | Glu | Asn | |

-continued

```
              180                 185                 190
gga aac tat gac tac tta atg ttt gct gat tta gac atg gat cac cct       720
Gly Asn Tyr Asp Tyr Leu Met Phe Ala Asp Leu Asp Met Asp His Pro
195                 200                 205                 210 gaa gtt gta gcc gag ttg aaa aac tgg gga aaa tgg tat gtg aac aca       768
Glu Val Val Ala Glu Leu Lys Asn Trp Gly Lys Trp Tyr Val Asn Thr
                215                 220                 225 acg aac gta gac gga ttt cgc tta gat gcg gtg aaa cat atc aaa tat       816
Thr Asn Val Asp Gly Phe Arg Leu Asp Ala Val Lys His Ile Lys Tyr
            230                 235                 240 agc ttt ttc cct gac tgg ctg tca tat gta cgt aat caa aca ggg aaa       864
Ser Phe Phe Pro Asp Trp Leu Ser Tyr Val Arg Asn Gln Thr Gly Lys
        245                 250                 255 aat tta ttt gcc gtc ggt gaa ttt tgg ggc tat gac gtc aat aaa ctg       912
Asn Leu Phe Ala Val Gly Glu Phe Trp Gly Tyr Asp Val Asn Lys Leu
    260                 265                 270 cat aac tac att aca aaa acg aat ggg gct atg tca tta ttc gat gcc       960
His Asn Tyr Ile Thr Lys Thr Asn Gly Ala Met Ser Leu Phe Asp Ala
275                 280                 285                 290 ccg ttg cat aac aac ttt tat att gct tca aaa tca agt ggt tac ttt      1008
Pro Leu His Asn Asn Phe Tyr Ile Ala Ser Lys Ser Ser Gly Tyr Phe
                295                 300                 305 gac atg cgt tat ttg ttg aat aac acg cta atg aaa gac caa ccg gca      1056
Asp Met Arg Tyr Leu Leu Asn Asn Thr Leu Met Lys Asp Gln Pro Ala
            310                 315                 320 cta gca gtc aca ctt gtt gac aac cat gac aca cag cct ggt caa tct      1104
Leu Ala Val Thr Leu Val Asp Asn His Asp Thr Gln Pro Gly Gln Ser
        325                 330                 335 ttg caa tct tgg gta gag cct tgg ttt aaa cca ctt gct tac gcc ttt      1152
Leu Gln Ser Trp Val Glu Pro Trp Phe Lys Pro Leu Ala Tyr Ala Phe
    340                 345                 350 att tta acg aga caa gaa ggg tat cca tgt gta ttt tac ggc gac tac      1200
Ile Leu Thr Arg Gln Glu Gly Tyr Pro Cys Val Phe Tyr Gly Asp Tyr
355                 360                 365                 370 tac ggc att cca aaa tac aat att cca ggc tta aaa agc aaa atc gat      1248
Tyr Gly Ile Pro Lys Tyr Asn Ile Pro Gly Leu Lys Ser Lys Ile Asp
                375                 380                 385 cca ctt ctt att gca cgt aga gac tac gca tac gga acg cag cgc gat      1296
Pro Leu Leu Ile Ala Arg Arg Asp Tyr Ala Tyr Gly Thr Gln Arg Asp
            390                 395                 400 tat atc gat cac caa gat att atc ggc tgg acg cgc gaa gga ata gac      1344
Tyr Ile Asp His Gln Asp Ile Ile Gly Trp Thr Arg Glu Gly Ile Asp
        405                 410                 415 gca aaa cca aac tct gga ctc gca gct tta att act gac ggc cct ggt      1392
Ala Lys Pro Asn Ser Gly Leu Ala Ala Leu Ile Thr Asp Gly Pro Gly
    420                 425                 430 gga agc aag tgg atg tat gta ggg aaa aga cat gct gga aaa gtg ttt      1440
Gly Ser Lys Trp Met Tyr Val Gly Lys Arg His Ala Gly Lys Val Phe
435                 440                 445                 450 tac gat ctc act gga aat cga agc gat aca gta aca att aac gca gac      1488
Tyr Asp Leu Thr Gly Asn Arg Ser Asp Thr Val Thr Ile Asn Ala Asp
                455                 460                 465 ggc tgg gga gag ttc aaa gtc aac gga ggc tcc gtc tca att tgg gtt      1536
Gly Trp Gly Glu Phe Lys Val Asn Gly Gly Ser Val Ser Ile Trp Val
            470                 475                 480 gcg aaa act tca aac gta aca ttt acc gtc aac aac gca acg aca gta      1584
Ala Lys Thr Ser Asn Val Thr Phe Thr Val Asn Asn Ala Thr Thr Val
        485                 490                 495 tat gga caa aac gta tat gtt gtt gga aat att cca gag cta ggg aac      1632
```

```
Tyr Gly Gln Asn Val Tyr Val Gly Asn Ile Pro Glu Leu Gly Asn
    500             505             510 tgg aac ata gcg aat gct att caa atg aca cca tct tct tat ccg aca    1680
Trp Asn Ile Ala Asn Ala Ile Gln Met Thr Pro Ser Ser Tyr Pro Thr
515             520             525             530 tgg aaa aca act gtt tcc ttg cct caa gga aaa gca att gag ttt aag    1728
Trp Lys Thr Thr Val Ser Leu Pro Gln Gly Lys Ala Ile Glu Phe Lys
        535             540             545 ttt att aag aaa gac agt gca gga aac gtt ata tgg gaa aac ata gcc    1776
Phe Ile Lys Lys Asp Ser Ala Gly Asn Val Ile Trp Glu Asn Ile Ala
        550             555             560 aat cga acg tat acg gtt ccg ttc tca tca aca gga tca tat acc gca    1824
Asn Arg Thr Tyr Thr Val Pro Phe Ser Ser Thr Gly Ser Tyr Thr Ala
        565             570             575 aac tgg aac gtg cca taa                                            1842
Asn Trp Asn Val Pro
580

<210> SEQ ID NO 6
<211> LENGTH: 613
<212> TYPE: PRT
<213> ORGANISM: Bacillus sp.

<400> SEQUENCE: 6

Met Ser Tyr Leu Lys Lys Val Trp Leu Tyr Tyr Thr Ile Ile Ala Thr
-30             -25             -20             -15

Leu Ile Ile Ser Phe Phe Thr Pro Phe Ser Thr Ala Gln Ala Asn Thr
        -10             -5              -1  1

Ala Pro Val Asn Gly Thr Met Met Gln Tyr Phe Glu Trp Asp Leu Pro
            5               10              15

Asn Asp Gly Thr Leu Trp Thr Lys Val Lys Asn Glu Ala Ser Ser Leu
20              25              30

Ser Ala Leu Gly Ile Thr Ala Leu Trp Leu Pro Pro Ala Tyr Lys Gly
35              40              45              50

Thr Ser Gln Ala Asp Val Gly Tyr Gly Val Tyr Asp Leu Tyr Asp Leu
            55              60              65

Gly Glu Phe Asn Gln Lys Gly Thr Ile Arg Thr Lys Tyr Gly Thr Lys
            70              75              80

Thr Gln Tyr Leu Gln Ala Ile Gln Ala Ala Lys Ser Ala Gly Met Gln
            85              90              95

Val Tyr Ala Asp Val Val Phe Asn His Lys Ala Gly Ala Asp Ser Thr
100             105             110

Glu Trp Val Asp Ala Val Glu Val Asn Pro Ser Asn Arg Asn Gln Glu
115             120             125             130

Thr Ser Gly Thr Tyr Gln Ile Gln Ala Trp Thr Lys Phe Asp Phe Pro
            135             140             145

Gly Arg Gly Asn Thr Tyr Ser Ser Phe Lys Trp Arg Trp Tyr His Phe
            150             155             160

Asp Gly Thr Asp Trp Asp Glu Ser Arg Lys Leu Asn Arg Ile Tyr Lys
            165             170             175

Phe Arg Gly Thr Gly Lys Ala Trp Asp Trp Glu Val Asp Thr Glu Asn
180             185             190

Gly Asn Tyr Asp Tyr Leu Met Phe Ala Asp Leu Asp Met Asp His Pro
195             200             205             210

Glu Val Val Ala Glu Leu Lys Asn Trp Gly Lys Trp Tyr Val Asn Thr
            215             220             225
```

-continued

```
Thr Asn Val Asp Gly Phe Arg Leu Asp Ala Val Lys His Ile Lys Tyr
            230                 235                 240

Ser Phe Phe Pro Asp Trp Leu Ser Tyr Val Arg Asn Gln Thr Gly Lys
        245                 250                 255

Asn Leu Phe Ala Val Gly Glu Phe Trp Gly Tyr Asp Val Asn Lys Leu
    260                 265                 270

His Asn Tyr Ile Thr Lys Thr Asn Gly Ala Met Ser Leu Phe Asp Ala
275                 280                 285                 290

Pro Leu His Asn Asn Phe Tyr Ile Ala Ser Lys Ser Ser Gly Tyr Phe
                295                 300                 305

Asp Met Arg Tyr Leu Leu Asn Asn Thr Leu Met Lys Asp Gln Pro Ala
            310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
        340                 345                 350

Ile Leu Thr Arg Gln Glu Gly Tyr Pro Cys Val Phe Tyr Gly Asp Tyr
355                 360                 365                 370

Tyr Gly Ile Pro Lys Tyr Asn Ile Pro Gly Leu Lys Ser Lys Ile Asp
                375                 380                 385

Pro Leu Leu Ile Ala Arg Arg Asp Tyr Ala Tyr Gly Thr Gln Arg Asp
            390                 395                 400

Tyr Ile Asp His Gln Asp Ile Ile Gly Trp Thr Arg Glu Gly Ile Asp
            405                 410                 415

Ala Lys Pro Asn Ser Gly Leu Ala Ala Leu Ile Thr Asp Gly Pro Gly
            420                 425                 430

Gly Ser Lys Trp Met Tyr Val Gly Lys Arg His Ala Gly Lys Val Phe
435                 440                 445                 450

Tyr Asp Leu Thr Gly Asn Arg Ser Asp Thr Val Thr Ile Asn Ala Asp
                455                 460                 465

Gly Trp Gly Glu Phe Lys Val Asn Gly Gly Ser Val Ser Ile Trp Val
                470                 475                 480

Ala Lys Thr Ser Asn Val Thr Phe Thr Val Asn Asn Ala Thr Thr Val
            485                 490                 495

Tyr Gly Gln Asn Val Tyr Val Val Gly Asn Ile Pro Glu Leu Gly Asn
        500                 505                 510

Trp Asn Ile Ala Asn Ala Ile Gln Met Thr Pro Ser Ser Tyr Pro Thr
515                 520                 525                 530

Trp Lys Thr Thr Val Ser Leu Pro Gln Gly Lys Ala Ile Glu Phe Lys
                535                 540                 545

Phe Ile Lys Lys Asp Ser Ala Gly Asn Val Ile Trp Glu Asn Ile Ala
                550                 555                 560

Asn Arg Thr Tyr Thr Val Pro Phe Ser Ser Thr Gly Ser Tyr Thr Ala
            565                 570                 575

Asn Trp Asn Val Pro
580
```